United States Patent
McNutt et al.

(10) Patent No.: US 10,872,684 B2
(45) Date of Patent: Dec. 22, 2020

(54) SYSTEM AND METHOD FOR MEDICAL DATA ANALYSIS AND SHARING

(71) Applicant: The Johns Hopkins University, Baltimore, MD (US)

(72) Inventors: Todd McNutt, Severna Park, MD (US); John Wong, Ruxton, MD (US); Theodore DeWeese, Towson, MD (US); Joseph Herman, Perry Hall, MD (US); Harry Quon, Rose Valley, PA (US); Kim Evans, Seattle, WA (US); Joseph Moore, Reisterstown, MD (US)

(73) Assignee: The Johns Hopkins University, Baltimore, MD (US)

( * ) Notice: Subject to any disclaimer, the term of this patent is extended or adjusted under 35 U.S.C. 154(b) by 547 days.

(21) Appl. No.: 15/039,677

(22) PCT Filed: Nov. 25, 2014

(86) PCT No.: PCT/US2014/067361
§ 371 (c)(1),
(2) Date: May 26, 2016

(87) PCT Pub. No.: WO2015/081086
PCT Pub. Date: Jun. 4, 2015

(65) Prior Publication Data
US 2016/0378919 A1    Dec. 29, 2016

Related U.S. Application Data

(60) Provisional application No. 61/909,937, filed on Nov. 27, 2013.

(51) Int. Cl.
*G16H 10/60* (2018.01)
*G16H 40/63* (2018.01)
(Continued)

(52) U.S. Cl.
CPC ............ *G16H 10/60* (2018.01); *G06Q 50/24* (2013.01); *G16H 40/63* (2018.01); *G16H 50/20* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 2005/0071189 A1* | 3/2005 | Blake | G06Q 50/22 705/2 |
| 2006/0095298 A1* | 5/2006 | Bina | G16H 40/20 705/2 |

(Continued)

OTHER PUBLICATIONS

International Search Report and Written Opinion in PCT International Application No. PCT/US2014/067361, dated Feb. 26, 2015.

*Primary Examiner* — Michael Tomaszewski
*Assistant Examiner* — Jay M. Patel
(74) *Attorney, Agent, or Firm* — Venable LLP; Henry J. Daley; Aziz H. Poonawalla

(57) ABSTRACT

A computer-implemented method may be provided for analyzing and disseminating medical information. The method may include steps performed by one or more processors including, receiving a plurality of patient medical data; aggregating the plurality of patient medical data, wherein access to patient private health information is restricted; receiving a query for medical information; analyzing the aggregated medical data based on the query; producing a result of the query based on the analyzing of the aggregated medical data; and transmitting the result of the query.

20 Claims, 11 Drawing Sheets

(51) Int. Cl.
*G16H 50/30* (2018.01)
*G16H 50/20* (2018.01)
*G06Q 50/24* (2012.01)

(56) References Cited

U.S. PATENT DOCUMENTS

| | | | |
|---|---|---|---|
| 2007/0118399 A1* | 5/2007 | Avinash | G16H 70/20 705/2 |
| 2008/0161661 A1 | 7/2008 | Gizewski | |
| 2008/0177578 A1* | 7/2008 | Zakim | G06F 19/3481 705/3 |
| 2008/0221923 A1* | 9/2008 | Shogan | G06F 19/00 705/2 |
| 2011/0153547 A1 | 6/2011 | McNutt et al. | |
| 2011/0225002 A1* | 9/2011 | Fackler | G06Q 50/22 705/2 |
| 2011/0257988 A1 | 10/2011 | Denekamp et al. | |
| 2011/0295887 A1* | 12/2011 | Palmese | G16H 20/40 707/769 |
| 2012/0078648 A1* | 3/2012 | Reiner | G06Q 50/22 705/2 |
| 2012/0290328 A1* | 11/2012 | McCallie, Jr. | G06Q 50/24 705/3 |
| 2012/0296675 A1* | 11/2012 | Silverman | A61B 5/7275 705/3 |
| 2014/0072192 A1* | 3/2014 | Reiner | G06F 19/321 382/128 |
| 2014/0257047 A1* | 9/2014 | Sillay | G16H 10/20 600/301 |
| 2015/0100341 A1* | 4/2015 | Pecora | G06F 16/9024 705/2 |

\* cited by examiner

SYSTEM AND METHOD FOR MEDICAL DATA ANALYSIS AND SHARING

RELATED APPLICATIONS

This is a national stage application under 35 U.S.C. § 371 of PCT/US2014/067361 filed Nov. 25, 2014, which claims the benefit of U.S. Provisional Application No. 61/909,937, filed Nov. 27, 2013, and is hereby incorporated by reference in its entirety.

TECHNICAL FIELD

The field of the currently claimed embodiments of this invention relate to creating an analytic pipeline to transform disperse medical data into accurate prediction models.

BACKGROUND

Accurate medical treatment relies on previous experience and data from clinical trials and model systems which inform and advance patient care. Clinical trials may represent care given to less than 5% of patients, take years for the results of the trials to become public, and may be controlled with more rigor than standard practice. Yet, clinical trials provide much of the guidelines for clinical practice and are typically focused only on a few aspects of treatment. Additionally, a significant proportion of dose constraints and expected toxicities are derived from historical experience and empirical data which is not always quantifiable. A vast amount of untapped knowledge is contained in data derived from routine clinical care.

Yet, commercial electronic medical records are not built to support the analysis required for accessing past experience. Furthermore, most current practices lack a uniform structured method of collecting clinical data, and few, if any, tools exist to evaluate and analyze these data in real-time. A technique to collect and provide readily accessible analysis of treatment plans and outcome data of prior patients may ensure the highest quality of treatments for the broadest community of medical patients.

SUMMARY

Aspects of the invention may involve systems, methods, and/or computer readable medium. In one embodiment of the invention, a computer-implemented method may exist for analyzing and disseminating medical information. The method may include receiving, by one or more processors, a plurality of patient medical data; aggregating, by the one or more processors, the plurality of patient medical data, wherein access to patient private health information is restricted; receiving, by the one or more processors, a query for medical information; analyzing, by the one or more processors, the aggregated medical data based on the query; producing, by the one or more processors, a result of the query based on the analyzing of the aggregated medical data; and transmitting, by the one or more processors, the result of the query.

In another embodiment of the invention, a system may exist. The system may include one or more mobile tablets for entering medical information; one or more storage devices, the one or more storage devices holding one or more databases, the one or more databases including one or more tables for storing and organizing the medical information, the one or more storage devices storing one or more instructions for analyzing and disseminating medical information; and one or more computers, wherein the one or more computers receive the medical information and store the medical information in the one or more databases, the one or more computers comprising one or more processors, the one or more processors operable to execute the one or more instructions, the one or more instructions comprising instructions for: receiving a query for medical information; analyzing the medical information; producing a result of the query based on the analyzing; and transmitting the result of the query.

In another embodiment, a non-transitory computer-readable medium may store computer-executable instructions. The computer-readable medium may include one or more instructions for: receiving a plurality of patient medical data; aggregating the plurality of patient medical data, wherein access to patient private health information is restricted; receiving a query for medical information; analyzing the aggregated medical data based on the query; producing a result of the query based on the analyzing of the aggregated medical data; and transmitting the result of the query.

BRIEF DESCRIPTION OF THE DRAWINGS

The foregoing and other features and advantages of the invention will be apparent from the following, more particular description of various exemplary embodiments, as illustrated in the accompanying drawings wherein like reference numbers generally indicate identical, functionally similar, and/or structurally similar elements. The first digits in the reference number indicate the drawing in which an element first appears.

DETAILED DESCRIPTION

Figure 1:
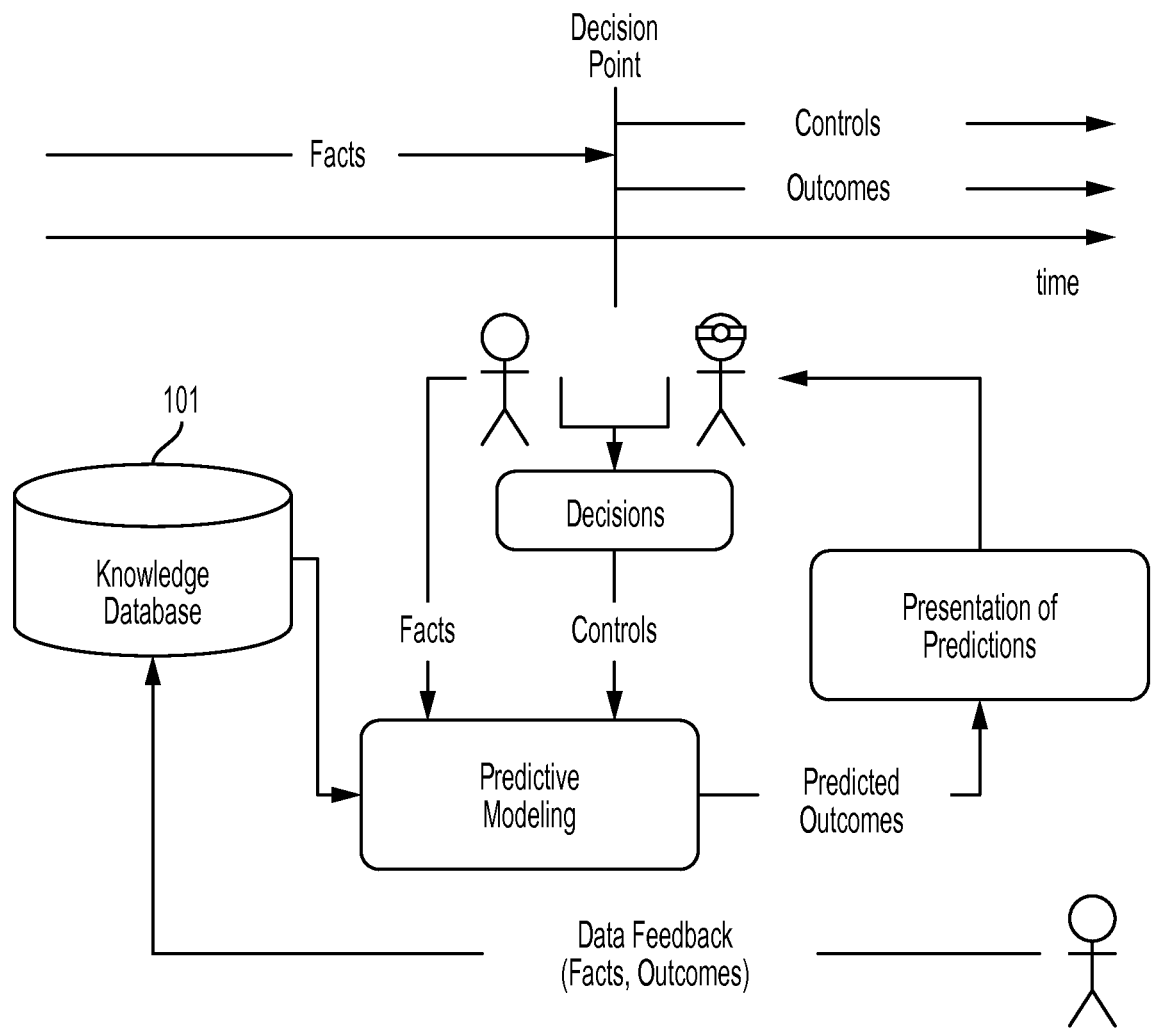
FIG. 1 depicts an example learning health system.

Exemplary embodiments are discussed in detail below. While specific exemplary embodiments are discussed, it should be understood that this is done for illustration purposes only. In describing and illustrating the exemplary embodiments, specific terminology is employed for the sake of clarity. However, the embodiments are not intended to be limited to the specific terminology so selected. A person skilled in the relevant art will recognize that other components and configurations may be used without parting from the spirit and scope of the embodiments. It is to be understood that each specific element includes all technical equivalents that operate in a similar manner to accomplish a similar purpose. The examples and embodiments described herein are non-limiting examples. Furthermore, the various features of the embodiments described herein may be extracted and/or combined to form new embodiments.

All references and/or publications cited herein are hereby incorporated by reference in their entirety. U.S. patent application Ser. No. 12/820,852 published as U.S. Patent Application Publication No. 2011/0153547 is hereby incorporated by reference.

As used herein, the term "a" refers to one or more. The terms "including," "for example," "such as," "e.g.," "may be" and the like, are meant to include, but not be limited to, the listed examples. The term "medical practitioner," for example, may refer to a medical doctor, a physician, a nurse, a nurse practitioner, clinician, physicist, researcher, a medical scientist, or other personnel in the medical field.

In an embodiment, treatment planning and clinical information about prior patients may be aggregated into one or more databases or other storage repositories. The aggregated data may then facilitate analysis and extraction of knowledge from prior courses of care. Through the use of web based interfaces, for example, past knowledge may be accessed and used to influence clinical decisions, quality, and/or safety of care for new patients. The aggregated information may be collected from and securely disseminated to multiple institutions, thereby facilitating analysis and extraction of knowledge across multiple institutions. The analysis may be presented in, for example, web pages designed to support specific questions that medical practitioners may request, using, for example, web-based controls enabling variations to the parameters of the questions.

In one example, quality radiation therapy (RT) may be based on previous experience as well as data from clinical trials and model systems which inform and advance patient care. In current practice, medical practitioners may study the effects of RT on patients and their disease through controlled clinical trials. However, trials may represent care given to a very small fraction (e.g., less than 5%) of patients, take years for results to become public, are typically controlled with more rigor than standard practice, and may be limited in the number of patients treated. A vast amount of untapped knowledge may be contained in data derived from routine clinical care which may treat many more patients than the clinical trials. Described herein are embodiments designed to compile and access the vast amount of data collected during routine care to improve clinical care at both the individual patient and practice level.

For example, the workflow in radiation oncology has multiple stages: from simulation to planning, from daily treatments and on-treatment visits to follow-up care. Several opportunities may exist to capture meaningful information that may be relevant to treatment success and prevention of toxicities. Most current practices lack a uniform structured method of collecting clinical data, and few tools, if any, exist to evaluate and analyze these data in real-time.

One embodiment may store and recall information about patients specifically designed for a medical specialty (e.g., radiation oncologists), for example, to assist in catalyzing the process of gaining experience, and may provide a toolset for validation of intuition or experience. These techniques may provide an interface to recall and present information that links a physician's experience to a system, for example, that may enhance the physician's ability to assess important clinical information and statistics. Techniques described herein may collect information consistent with capturing the experience of the physician without being intrusive to the clinical practice. For example, tablet based patient and physician directed input may significantly aid and improve data collection without being intrusive.

In another embodiment, data may be presented to the patient to empower the patient to be an active participant in the decision making process which is an important long-term goal of personalized medicine. Refining data analysis to include prior patients with similar clinical parameters to the current patient and enabling display of outcome related information may help guide the patient and physician through the decision making process and may help realize a goal of enhanced personalized care.

In one embodiment, radiation oncology practice, for example, may be enhanced by peer to peer sharing of experience (e.g., shared data on treatment and outcomes) across multiple institutions through professional collaborations. Advancing practice changing knowledge through incorporating complex dosimetric data with outcome analytics may be substantively enhanced with multi-institution data-sharing. Importantly, sharing data may be particularly advantageous for the management of rare to uncommon histologies. Sharing outcome data on all treated patients (e.g., those on and off clinical trials) across institutions will lead to further knowledge gain and improvements in patient care in radiation oncology.

Readily accessible analysis of treatment plan and outcome data of prior patients may, for example, ensure higher quality of treatments for the broad community of patients. A comprehensive database may allow for the first time, a quantitative means of measuring the quality of medical practices and the ability to more accurately predict the expectations for new patients based on the outcomes of prior patients.

In one embodiment, a platform, for example, titled "Oncospace," may function to capture medical information (e.g., radiation oncology information) during the clinical workflow, that platform may use the captured data for safety, quality, quantitative outcomes and toxicity prediction, and patient education in clinical practice. The design of the system may include, for example, an analytical database structured to support easy retrieval of clinical knowledge. In addition, a web-based portal to the database may provide secure access, and the opportunity for multi-institutional deployment.

Data Collection

Clinical information about patients in the clinical setting may be collected for use in future analysis. However, current electronic medical records are geared towards the generation of text based clinical documentation. Additionally, regulatory requirements are geared towards certain language being included in documentation. What is needed is a technique to collect information on patients that is consistent with capturing the experience of the patient that is not intrusive to the clinical practice. In another embodiment, an oncology information system, such as MOSAIQ-Elekta, of Sunnyvale, Calif., may be used to manage patients and to store clinical information for permanent electronic records. In addition to managing the patient and physician schedules, this system may allow specification of the disease (ICD-9) and input of, for example: staging information; vitals and lab values; medications and chemotherapy; the radiation therapy prescriptions; and treatment plans and record of delivered treatments. Data may be collected directly from the treatment planning system and the oncology information system (OIS). Stored medical data may include, for example, disease and staging; vital signs and lab values; medications and chemotherapy; RT prescriptions and plans. A patient observation module may also be provided that facilitate structured data collection in the clinical setting using user-defined forms for the entry of observational data prospectively during the patient-clinician encounter to assist in generating clinical documentation. The patient observation module may be customized to support on-treatment assessments and follow-up visits. This may provide structured data collection to be integrated into the clinical process for all physicians. Mobile devices such as iPads and tablet PCs may offer an opportunity to improve the clinical workflow while also incorporating structured data collection into the process.

For example, the care team in a typical radiotherapy practice may be as simple as a nurse and physician pair in a private practice setting, or may be as complex as having clinical assistants, nursing, mid-level providers, residents and attending physicians managing a clinic schedule. In either case, multiple care providers may capture information about the patient with the goal of including it in the electronic medical record.

Patients undergoing radiotherapy, for example, may have 3 types of encounters with their physicians: initial consults, weekly on-treatment visits, and/or follow ups. The data collection workflow for each visit may include: vital signs, labs, medications, quality of life surveys, toxicity or symptom assessments, physical examinations, and an impression and plan. Each of these items may be captured by different members of the care team.

Current exam rooms, for example, are often equipped with a single computer with access to the electronic medical record. This may pose its own challenges as different users may have to login at different times throughout the visit to complete their part. Additionally, the position of the computer within the exam room must be place so not to detract from the patient-physician encounter. Accordingly, by using a mobile tablet style device members of the care team may be able to complete their clinical day managing the patient visits while minimizing the impact on the clinical workflow to ensure that the patient-clinician interaction is not impeded by the system.

In one embodiment, a website solution may be accessed by iPads and other tablet devices that communicate directly with a MOSAIQ database. The care team members may manage their daily patient schedule with the mobile solution and capture structured clinical data during the patient encounter. Furthermore, the structured data may then be used to build the clinical note saving them time in post-visit dictation.

The mobile solution may provide convenient access for physicians and may be designed for them to complete specific clinical tasks on mobile devices such as iPads and have the records stored into the MOSAIQ system as if the task was completed in MOSAIQ directly. The mobile device and accompanying web-based infrastructure may allow the physician to complete his/her clinical day from the mobile device while easily moving from room to room and being able to quickly review the patient summary before entering the room with the patient. For example, on a clinical day, a physician may quickly navigate quickly to each patient directly from their electronic daily schedule. For the selected patient they may perform the following tasks, for example:

1. Quickly review the patient summary providing a one page treatment summary for a specific patient. The summary may include, for example, diagnosis, prescriptions, assessments, medications, clinical trial, treatment planning documents, and/or a schedule of future visits.

2. Perform clinical assessments through a web page generated from a selected assessment view as defined in, for example, MOSAIQ (e.g. Head and Neck On-Treatment Visit Assessment). The page may have numeric entry, checkboxes, pull down menus and text and note fields created based on the observation definitions in MOSAIQ. In addition, mobile devices with voice recognition may be used to speak into the text fields.

3. Perform patient Quality of Life assessments by enabling patients to enter quality of life assessments directly into MOSAIQ assessments while protecting privacy of other patients.

4. Automatically generate clinical notes for a specific patient using a site-specific template and logic to build notes from structured data collected during clinical assessments. This note may be transferred to another system for additional edits if needed depending on the clinical electronic environment.

In addition, there may be utility pages that allow physician's to perform tasks related to treatment planning workflow management. The following tasks may also be performed on, for example, smart phones or tablets:

1. Quick review of the physician's clinic schedule to identify patients that may have arrived and are ready to be seen.

2. Review the physician task list including open Quality Check List items and/or documents that may need approval.

3. Remote plan and prescription approval. This page displays the unapproved prescriptions and treatment documents for a specific patient and allows the user to view and approve those items. Approval may only be permitted, for example, if the logged-in user has appropriate permissions in MOSAIQ and is flagged as the reviewer. A direct link to the page may be sent by the requesting person to the physician's phone via SMS text or email, allowing the physician to quickly link to the page, review the plan and prescription and approve it for treatment, for example.

The web pages may be setup to allow the care team to manage the day from the physician's schedule. Navigation to each patient may be done by simply taping on their schedule item. The schedule list may identify which exam room the patient is in and whether or not they have arrived. Prior to rooming the patient, their vitals may have been taken and may be available for viewing on the mobile device.

The care team members may be able to view a summary of the patient which may include the patient's: vitals, medication list, radiation dose summary, clinical assessments from prior visit and/or prior notes.

Clinical assessments may be added by selecting the appropriate form. When the assessment is added a web form is created that creates entry widgets that match the particular data item identified in the MOSAIQ form, for example. If it is a selection list that contains less than certain number of entries (e.g., 4) a check box list may be created. If it contains more than the number (e.g., 5 or more) a pull down menu may be created. If it is a numeric of text entry a basic text entry field may be created. Dates may have a calendar entry field. Each entry may also have a validator that low (yellow) and high (red) warning flags for entries that exceed the warning levels specific in MOSAIQ. The form may contain data entry fields that are targeted for the clinical environment to minimize the number of entry fields displayed.

In another embodiment, the impact of data collection on the clinical workflow may be minimized to ensure that the patient-clinician interaction is not impeded. Web-based forms may be designed for use on mobile tablets to perform clinical and quality of life assessments without overly impeding the medical practitioner interaction. For example, point of service collection may be facilitated with tablet (e.g., iPad) forms linked to the OIS. The web-based system may allow further customization to tailor the workflow to the Nurse-Resident-Attending encounter with the patient. For example, physicians may manage their daily patient schedule with the mobile solution and capture clinical data during a patient encounter. Furthermore, the data may then be used to build one or more clinical notes, saving medical practitioners' time in post-visit dictation.

Collection of medical data may include, for example, multi-modality (e.g., CT, x-ray, PET/SPECT, MRI, DCE-MRI, diffusion-weighted MRI, and/or Ultrasound) imaging. These multi-modality images may be used by image processing tools for target definition, automatic feature extraction, and/or other quantitative imaging metrics as meta-data for efficient query and analysis. Additionally, pre-, intra-, and post-treatment imaging metrics and non-imaging data may be used as bio-markers for treatment optimization and intervention. The multi-modality imaging data may help to support decision making for the treatment of patients. For example, the extraction of quantitative metrics of anatomic, functional, and biological imaging information in a structured manner may complement the current outcome and dosimetry information for early treatment assessment, intervention, and outcome prediction. Additionally, the multi-modality imaging data may assist, for example, in assessing tumor volume reduction during treatment and in assisting in adaptive radiation therapy.

In one embodiment, toxicity and 3D dose may be stored to enable a better understanding of the relationship between dose and normal tissue complication probability (NTCP). Though computers struggle with understanding textual data, they are very capable of understanding complex multi-dimensional data that often is not translatable to easy publication, or to be considered by the human brain. For example, one might request information such as, "What is the risk of xerostomia given this 3D dose distribution, the patient diagnosis, history and baseline function and concurrent therapies?" and an embodiment could search the database and find similar patients with similar dose distributions and characteristics FIG. 1 depicts an example learning health system. The learning health system of FIG. 1 may use a knowledge data base to perform predictive modeling and present the predictions in a form that enables physicians to easily navigate and analyze the system for a knowledgebase of prior patient experiences and facilitate translation of that knowledge into clinical decision making and quality assurance for new patients.

FIG. 1 may include a knowledge base 201 of prior patient data, a set of predictive models, and a means to present the predictions to care providers and patients in a way to assist them in decision making. The system may learn with every new patient's data that is fed back into the system.

In an example learning health system there may be three fundamental types of data about the patient. The data types may be dependent on the moment of the decision point in the course of care for the patient.

Facts or fixed data are information about the patient that cannot change. Examples are gender, race, diagnosis and genetics. Also included are facts that have already happened, such as baseline toxicity, or prior medications that have been used, or measured disease response.

Controls are what we can change or adjust for a patient during the course of care. This includes symptom management options such as future medication or nutritional support. It also includes any changes that can be made to treatment such as modifying the treatment doses.

Outcomes are those data that represent the measures of disease control, treatment related toxicities, and the quality of life of the patient. These are measures of how well the patient has been cared for and may represent areas for improvement in a learning health system.

Patients are on a timeline as they go through treatments. As they progress with treatment (time), both control data and outcome data become factual data. At the midpoint of therapy, any medications used or toxicities experienced, or disease response measures become facts.

One of the goals of a decision support system is to use the factual and remaining control data (or feature vector) to predict the outcomes for patients. Then to explore the remaining control data to see how changes in the control change the prediction of the outcomes. The decision support is thus to help decide how to modify control variables to get the best outcomes for the individual patient.

In radiotherapy, there are many control variables. For example, the radiation dose can be modified, symptom management medications, nutritional support (e.g. feeding tube), and physical therapy are all options.

An embodiment of the learning health system has the depth, granularity and numbers of data necessary to make predictions of outcomes with enough statistical power to be safe for a patient. The system depends on the data from prior patients to make predictions for new patients. The knowledge must be contained in the data with sufficient detail to make critical decisions.

In an example model of dose vs toxicity, control data may be a radiation treatment plan which is a 3D dose distribution delivered to the patient. The facts may be the patient anatomy, the tumor and target regions for treatment as well as patient history, concurrent therapies, baseline function and diagnosis. The outcomes may be disease status, treatment related toxicities, and quality of life. A goal may be to establish a learning health system that allows for better decisions on a dose distribution that controls the disease while minimizing the toxicity.

Data Aggregation

Existing clinical information and treatment planning systems may not be designed to aggregate medical data for analysis and experience sharing. To overcome this limitation, for example, clinical experience may be stored in a relational database as described below in FIG. 1 to house medical data (e.g., RT data).

Figure 2:
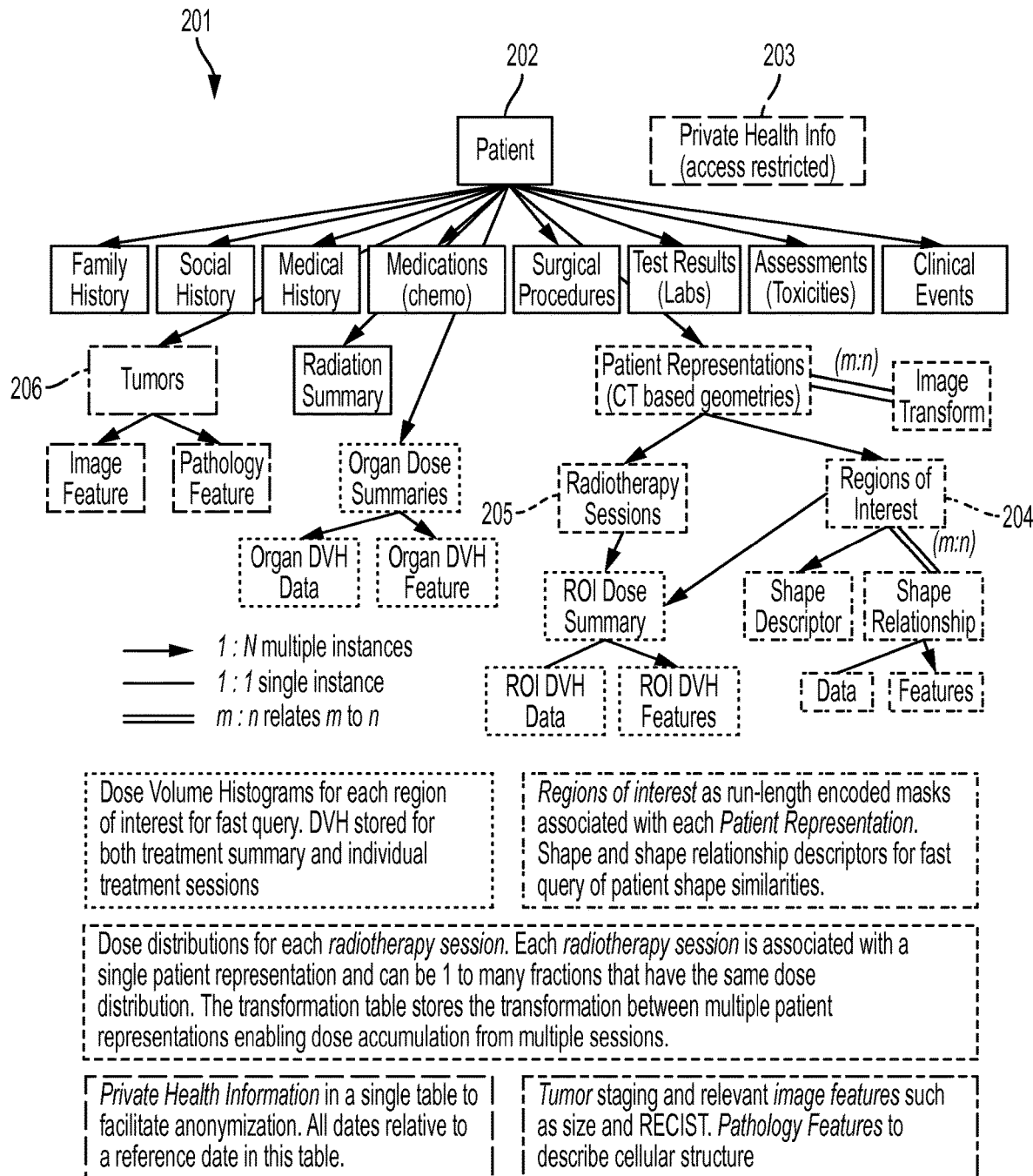
FIG. 2 displays a sample database schema showing relationships between various data tables.

FIG. 2 displays an example database schema 201 primarily centered around patient table 202. The data tables may be arranged, for example, to support patient geometry, targets and organs at risk (OARs) and their spatial relationships, dose distributions and dose volume histograms (DVHs), toxicities, diagnosis and disease progression, chemotherapy and medications, laboratory values, patient histories and demographics.

Private health information (PHI) may be isolated in a single PHI table 203. PHI table 203 may be a single table per institution. PHI table 203 may enable the database to be anonymous when PHI table 203 is removed or when access to PHI table 203 is restricted. In addition to standard private health information, PHI table 203 may store a reference date for which all other dates in the system may be relative to. The reference date may be, for example, the first day of treatment or other reference date. If the reference date is the first day of treatment, then the other dates in other tables may be in days from first treatment.

In addition to patient table 202 and private health information 203 table, database schema 201 may link the patient table 202 to one or more other database tables such as, for example, family history, social history, medical history, medications, chemotherapy treatments, surgical procedures, test results, assessments, toxicities, clinical events, tumors 206, radiation summary, organ dose summaries, patient representations, and/or CT based geometries. The patient representations table may be linked to, for example, one or more of the following tables: image transform, radiotherapy sessions 205, and regions of interest 204. The regions of interest table 204 may be associated with, for example, one or more of the following tables: shape descriptor and/or shape relationship. The shape relationship table may have associated data and feature tables. Both the regions of interest table 204 and the radiotherapy session table 205 may be associated with a region of interest dose summary table which may be associated with a region of interest dose volume histogram data table and a region of interest dose volume histogram features table. The organ dose summaries table may be associated with, for example, organ dose volume histogram data table and organ dose volume histogram feature table. The tumors table 206 may be associated with, for example, one or more image feature tables and pathology feature tables.

The shape of the lines connecting the tables in database schema 201 indicates the connection between the tables. For example, a single line between two tables indicates 1:1 single instance, an arrow between two tables indicates 1:N multiple instances, and a double line indicates m:n which relates m to n. For example, private health information table 203 is a single table with a 1:1 relationship to patient table 202. This 1:1 relationship may assist in facilitating anonymity and protection of identifying information. Regions of interest table 204, for example, may be stored as run—length encoded masks associated with each patient in patient representations table. Regions of interest table 204 may have a m:n association with shape relationship tables and a 1:N association with shape descriptor tables. The shape descriptor and shape relationship tables may provide for a fast query of patient shape similarities. Dose volume histograms for each region of interest may also provide for a faster query than what is currently available. In current systems, for example, medical data may be stored in DICOM RT with three dimensional dosing information and three dimensional shape and the dose volume histograms must be calculated. In one embodiment, a query may be improved as no raw three dimensional data requires calculation before answering the query. For example, a query may ask, for all patients with problem X, what was the best dose and the answer may be returned without a timely data calculation.

Dose volume histograms may be stored for both treatment summary and individual treatment sessions. Often, in treating a patient, more than one treatment plan or sessions may be prescribed. For example, in one session a large volume at a dose level may be treated for a number of times (e.g. 23 times), in another session a smaller target may be treated for a different number of times (e.g., 5 times). In this case, a query could provide the total dose delivered (e.g., treatment summary) or the separate doses delivered (e.g., individual treatment sessions).

Dose distributions may be stored for each radiotherapy session in radiotherapy session table 205. Each radiotherapy session in radiotherapy session table 205, for example, may be associated with a single patient representation and may be 1 to many fractions that have the same dose distribution. The image transform table may store the transformation between multiple patient representations enabling dose accumulation from multiple sessions. For example, with on the session dose and the number of sessions, the total dose may be computed. Tumors table 206, for example, may be associated with tables to store tumor staging and relevant image features such as size and response evaluation criteria in solid tumors (RECIST). The pathology features table, for example, may describe the cellular structure of a tumor listed in tumors table 206.

Received clinical data (e.g., data from MOSAIQ) may be transferred through a direct extract, transform, and load (ETL) process between databases. In the ETL process, some data may be directly transferred, where other information may be derived from the clinical data in the ETL process. For example, PSA scores may be directly transferred from the lab result data. Alternatively, diagnosis PSA or pre-treatment PSA score may be calculated from the PSA score closest to and before the first date of treatment. Other data may include the raw data, acute toxicity, or late toxicity (e.g., 3 months after finished treatment). Dates may be converted to be relative days from a chosen reference date (e.g., first day of treatment). The ETL process may involve analyzing raw data from clinical systems and converting the information into meta-data to be stored and available for querying.

For treatment planning information, a significant amount of processing must be performed to populate database schema 201. In an embodiment, a proprietary treatment planning system interface (e.g., Pinnacle3, Philips—Madison Wis.) and a DICOM RT import utility for ETL of the planning information, for example, may be used. Database schema 201 may support multiple patient representations and the transformations between the multiple patient representations (e.g., deformable or rigid) to support dose accumulation from multiple RT courses, or daily variations in the patient that can be accounted for dosimetrically. Ultimately, an accurate determination of actual dose delivered to the patient may be stored.

In one embodiment, the platform design may encourage data sharing across institutions while protecting patient privacy. The data may be collected and stored at each institution and then shared with other intuitions. By allowing each institution to control its own data, institutions may have unfettered access to their own data while controlling information that is accessible by other institutions. The design overcomes the current issue of institutions being reluctant to share data as the source of the data is preserved.

Figure 3:
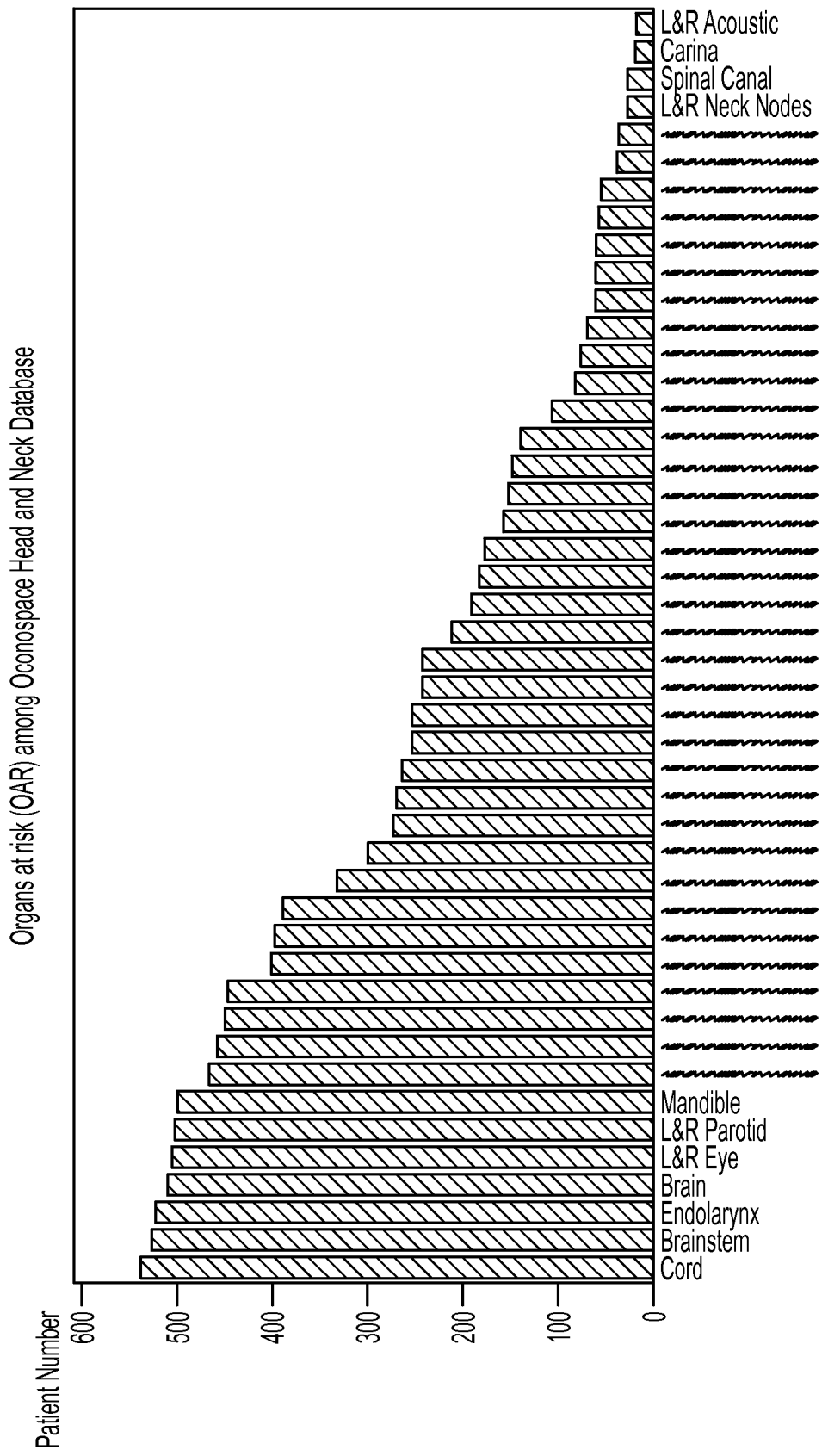
FIG. 3 displays illustrates example data showing the number of organs at risk that have full radiation dosimetry and shape relationships to target volumes within a database.

FIG. 3 shows an example graph of an inventory of anatomical structures defined with full dosimetry. This data collected may have the depth and granularity needed to begin to address models of how the 3D dosimetry relates to toxicities in patient population.

Predictive Models

Medicine may pose several challenges to data science. For example, a considerable amount of relevant data is, in general, subjective as it is dealing with clinical assessments of well-being and quality of life. There is also inherent uncertainty in the data. There are sampling issues as only certain time points are assessed. The presence of highly correlated variables also poses a problem.

Fayyad, et al. (*From Data Mining to Knowledge Discovery in Databases*, American Association for Artificial Intelligence, Fall 1996) introduced what is generally considered the fundamentals of the process for knowledge discovery in databases (KDD). In the case of health-care, data is generally from electronic health records (EHR), or other components within hospital information system.

Fayyad, et al. divides KDD into nine steps: (1) understanding the problem domain and the previous work in the area; (2) selecting a target dataset; (3) data cleaning and preprocessing; (4) data reduction and projection; (5) matching the knowledge discovery goals with a data mining approach; (6) exploratory analysis with hypothesis and model testing; (7) data mining; (8) interpreting results; and (9) acting on discovered knowledge.

KDD primarily addresses situations where the original data is unstructured and stored in relational database systems. In an embodiment, structured and unstructured data may be distinguished based on the level of preprocessing required. For example, data fields such as height, weight, name, name, address, etc. may be structured fields. Images, free-text, dose grids, etc. may be unstructured data. Unstructured data may be stored in files (e.g., not relational database management systems (RDBMS)). When unstructured data are within a RDBMS, they may be stored in binary large object (BLOB) or character large object (CLOB) fields.

The emerging area of data science addresses the requirements unstructured data imposes. An embodiment of a data science platform may utilize an analytic sandbox that may be separate from the organizational data repository. Due to the lack of statistical proofs of confidence in most data mining algorithms, data science modeling may involve "failing enough," that is experimenting with enough models and data transformations to develop assurance in the superior models that emerge possessing true predictive advantages. The analytic sandbox allows for conducting research without risking the original data stores.

In an embodiment, a step in machine learning may be to represent a patient as a set of features referred to as a feature vector. Features may be transformations of, for example, the raw DVH dosimetric and spatial data. A set of feature vectors (e.g., patients) may be referred to as a dataset. Feature selection may be a process of selecting the most informative features from an initial set of candidates.

A trainer algorithm may use a set of feature vectors (e.g., training data) to learn (e.g., train) a model. From a workflow perspective, the trainer receives the vectors as input and outputs a model. Training data vectors will contain outcome as one of the features. In the case of NTCP modeling, the model the trainer learns will be a classifier. The classifier accepts new feature vectors, and outputs a prediction of the presence of the complication. The trainer algorithm and the set of models it can learn together form a machine learning technique.

A machine learning approach has a number of benefits. Unlike animal models, the results are directly applicable to human patients. The research is less costly and labor intensive than clinical trial, or manually segmenting images outside of the clinical workflow. Further, machine learning offers the possibility of personalized medicine by incorporating features reflecting medical history, chemotherapy, demographics, etc.

A drawback of machine learning may be that the models are data driven and not based on the underlying biological process. Accordingly, clinical interpretation of machine learning results is essential. Accordingly, the machine learning methods may be assisted with known biological processes.

The Presentation of the Prediction and Decisions

In an embodiment, the presentation of the predictions from the predictive modeling may be a part of a learning health system. The decision support system may present the predictions, while also offering some ability to adjust the control variables to see how the predictions change to potential outcome of the patient.

For example, a prediction of a 40% risk in grade 2 xerostomia may be given. Then, how a change in dose distribution could impact the prediction may be presented. The presentation display may provide, as part of the framework, facts and possible control variables of the new patient. The decision support system may be interfaced with clinical systems to easily provide full radiation dosimetry and clinical factors to the predictive modeling tools.

Data Presentation

A website such as the Oncospace website, for example, may provide access to the database through tools such as a web browser. For example, the developed code base may be used to write a new web page for other institutions; with the institutions sharing the same database design and common data dictionary. The website may provide a platform for developing tools to navigate through the data to directly answer clinically relevant questions. Web pages may be developed to answer specific clinical questions. The website may be also used to develop tools that can influence the safety and quality of care for new patients.

In an embodiment, patient safety may be addressed by alerting users (e.g., medical practitioners, patients, etc.) when an individual patient's treatment information deviates from similar patients in the database.

Quality may be improved by predicting, based on the stored data, how well a particular patient may respond to a treatment plan, and having the medical practitioner seek to achieve it. The prediction may involve reviewing stored data on similar patients. Patients that are similar may include may include, for example, patients with one or more of the same or comparable disease, diagnosis, pathology, treatment site, staging, age, sex, demographics, physician, toxicity (e.g., grade 3), geography, medications, lab scores, treatments, prescriptions, doses, date of treatment, etc. As more research and clinical data is added, similarities between patients may become better defined.

Personalization of care may be achieved when medical practitioners and patients review results of similar patients and make decisions based on data specific to the patient's needs.

In one embodiment, the following queries relating to clinical decisions for safety and quality of care may be presented by a medical practitioner and provided with a response based on the collected data.

A. For patients with a selected diagnosis and disease histology, what is the distribution of dose-fractionation prescribed?

B. For a selected toxicity and organ at risk, display the dose volume histograms and colorize them by the maximum toxicity grade of the patient. For a specified organ at risk volume percentage, graph the mean dose received for each toxicity grade.

C. For a selected organ at risk and percent volume, find the lowest dose achieved from all patients whose percent volume is closer to the selected target volume.

D. For a selected diagnosis, toxicity and treatment, display the aggregate trend in toxicity from start of treatment (acute) through several year follow-up (late).

Data Sharing

Figure 4:
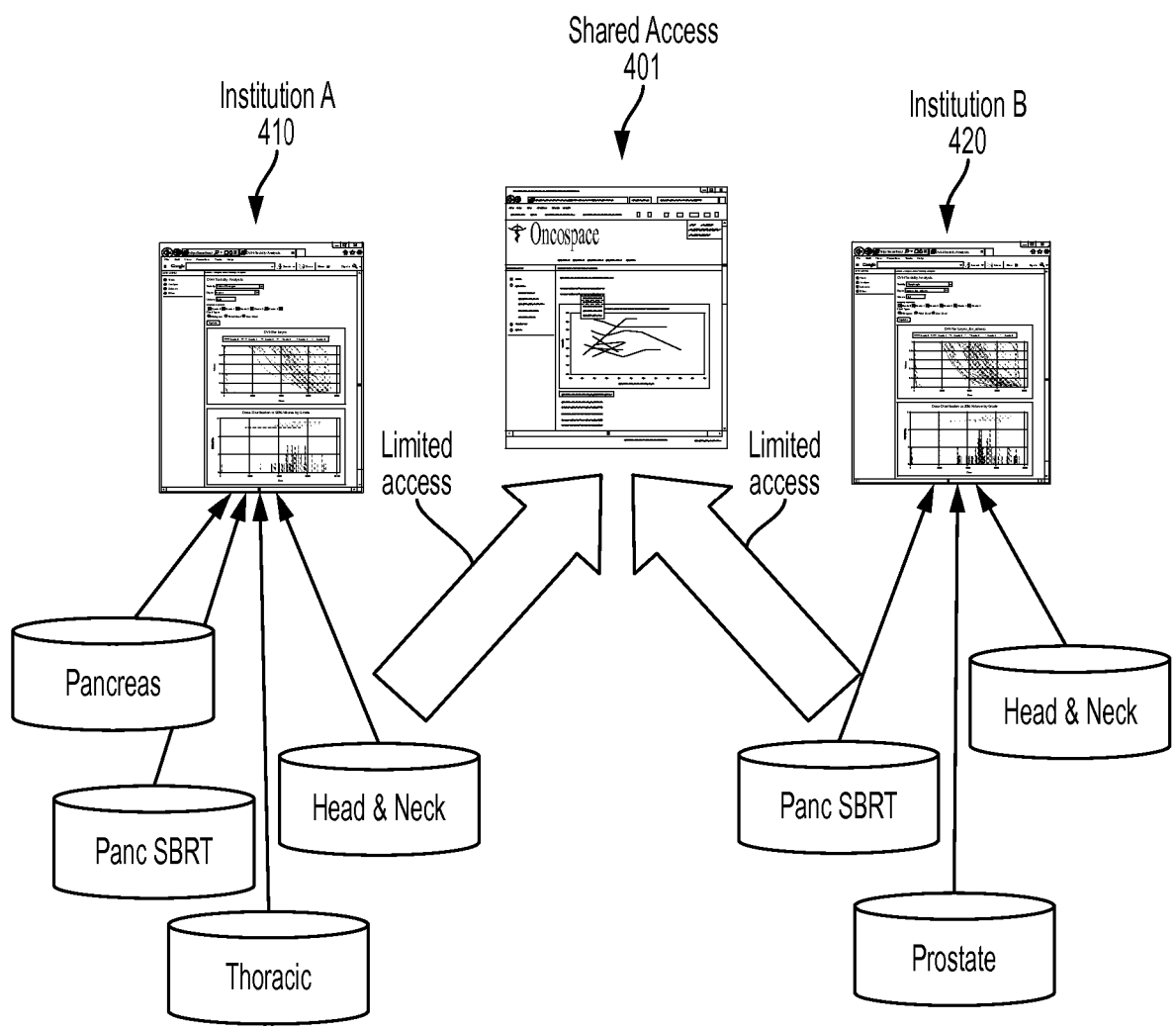
FIG. 4 illustrates an example of data sharing between institutions.

FIG. 4 illustrates an example of sharing of data between institution A 410 and institution B 420. In particular, a federated model is shown that may allow each institution to have full control over their own data, while also allowing sharing of limited data between institution A 410 and institution B 420 via shared website 401.

In one embodiment two or more participating institutions (e.g., 410, 420) may maintain their own databases (e.g., the Oncospace database) with the defined database schema 201. The databases may be populated via the extract, transform, load (ETL) process from the institution's specific clinical systems and any new information about patients may be updated locally at the site. Webservices 401 (e.g., the Oncospace website) may then communicate with the grid of databases as if they were a single database.

Accordingly, a user of the system may have access to multiple institution's data without the complications of data transfer, thus facilitating data sharing among the institutional community. The database may be designed such that inter-institutional access may be de-identified by restricting access to or removing the PHI table 203 in the database. Further restrictions to inter-institutional access may be defined such that only aggregated results of queries may be displayed depending on the data sharing relationships established among participating institutions. These restrictions may be controlled, for example, through web site design, data access permissions, and/or query approval.

Results

The following models, utilize the data for various improvements in care for patients, identify example embodiments of how the data may be used in a clinical setting:

Diagnosis vs Prescription

In RT, for example, peer review may be used as a means of detecting potential errors in treatment prescription and plans for patients (e.g., verifying a prescription regimen). An embodiment of the current invention may provide for the verification of the correct prescription for a particular diagnosis. For example, Oncospace may be used to assist in this process by identifying when a particular prescription deviates from what is commonly employed for previous patients with the same diagnosis, pathology, and/or treatment site.

Figure 5:
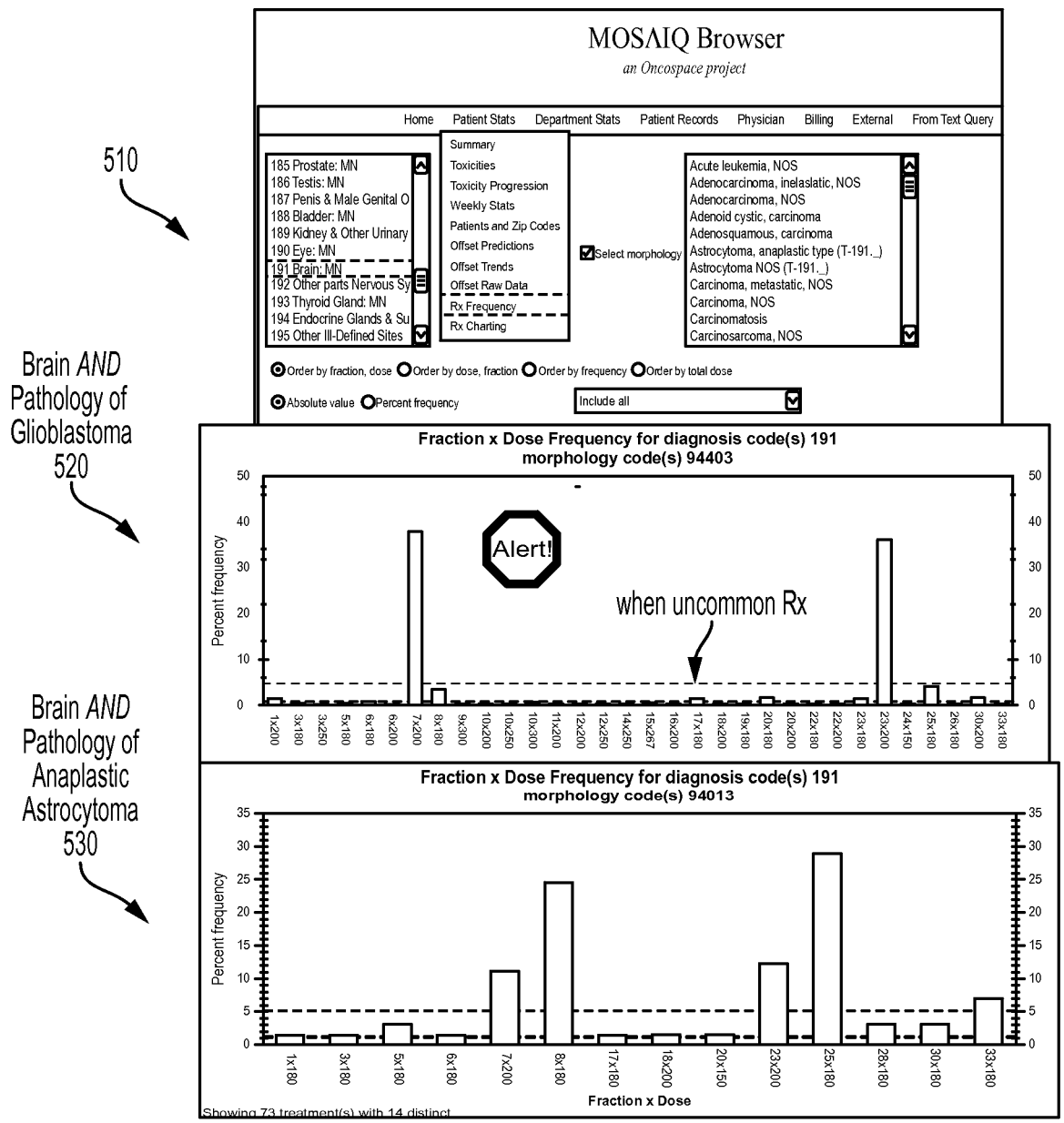
FIG. 5 displays an example query result showing frequency of dose fractionalization used for selected diagnosis and pathology.

FIG. 5 displays example graphs 520 and 530, for frequency of each dose fractionation used after selecting a diagnosis and pathology in browser entry field 510. The supplied data may be used as a basis for alerting medical practitioner when, for example, uncommon prescriptions are being used. In particular, the graphs display various prescriptions used for select diagnosis and pathologies. Prescriptions that deviate from the norm may be highlighted for further scrutiny at the time the prescription is entered and/or during peer review. This is akin to drug-drug interaction alerts when electronically prescribing medications. FIG. 5 displays browser entry fields 510 that allow a user to select, for example, an organ (e.g., prostrate, eye, brain, thyroid, etc.), a report type (e.g., toxicities, toxicity progression, patients and zip codes, offset predictions, prescription frequency, prescription charting, etc.) and a pathology (e.g., leukemia, adenocarcinoma, glioblastoma, anaplastic astrocytoma, etc.) and then display corresponding graphs (e.g., 520, 530) depending on the values selected in entry field 310.

Dose vs Toxicity

Normal tissue dose constraints may be determined based on clinical experience and occasionally clinical trials which may be reduced to a set of relative constraints on a DVH or alternatively volumetric constraints. These points may be selected based on toxicity assessments of a select group of patients. An embodiment of the invention (e.g., Oncospace) may assist in navigating the DVH and toxicity information by providing an interactive tool for medical practitioner to gain a better understanding of the dose-toxicity relationship for the clinical practice.

Figure 6:
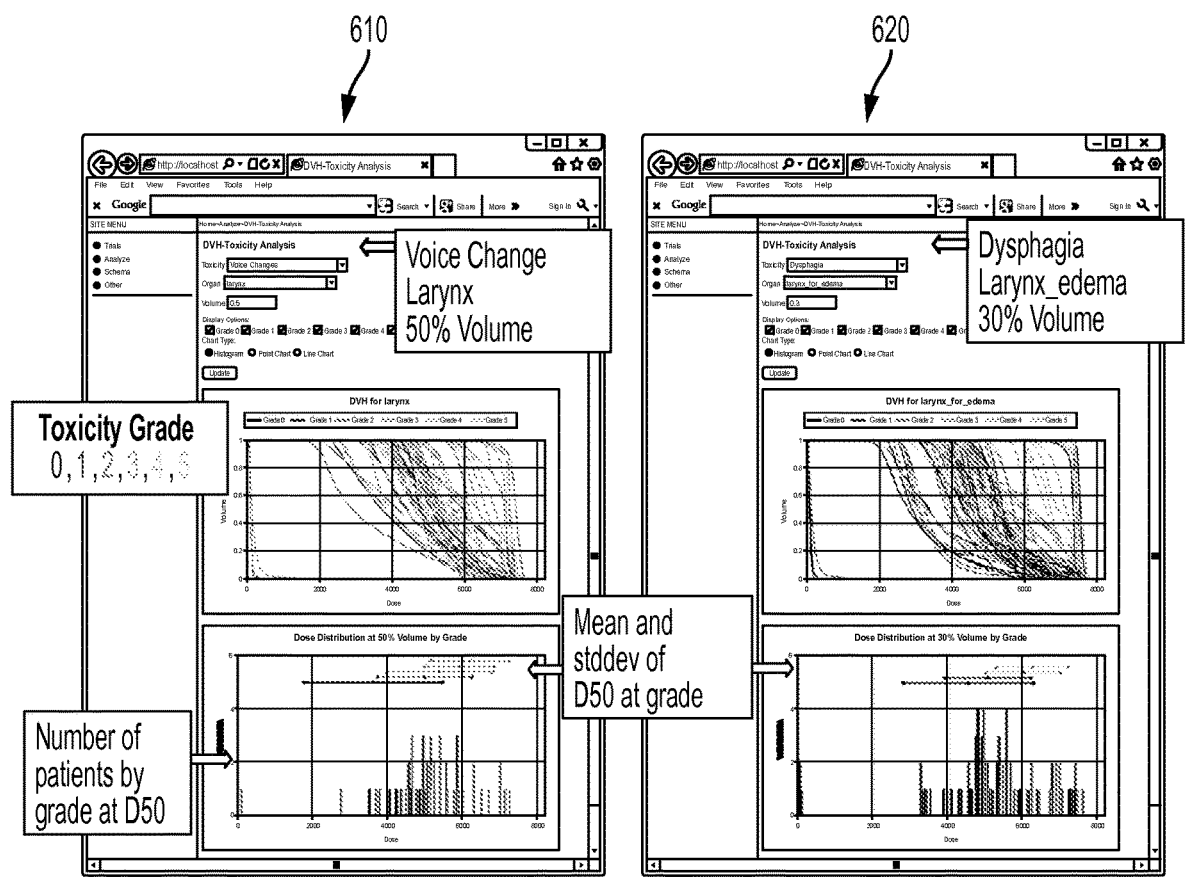
FIG. 6 displays an example query result showing dose-volume histogram distinguished by the maximum toxicity grade of the patient, and an example graph of the mean dose, across patients, received for each toxicity grade.

FIG. 6 displays example pages showing how a medical practitioner may select, for example, a particular toxicity, OAR and percent volume of that OAR. Graphs 610, 620 then display the DVH's color coded, for example, by maximum toxicity grade experienced by the patient and build a display of patient distributions of a particular maximum grade as a function of dose to the specified percent volume of the OAR. Graphs, such as graphs 610 and 620, for example, may allow medical practitioner to determine where a particular patient's DVH lies among all the previous similar patients that were treated to explore the risk of toxicity of the new patient. FIG. 6 shows, for example, that for a selected toxicity and OAR, the DVH may be displayed and, for example, colorized by the maximum toxicity grade of the patient, and for a specified OAR volume percentage (% V), the mean dose may be graphed across patients received for each toxicity grade. The displayed trends may identify correlation between dose and toxicity. The medical practitioner may select a chart type of a histogram, point chart, or line chart and may select grade 0-grade 5. In particular, graph 610 displays selecting a toxicity of voice change, an organ at risk as the larynx, and a volume of 50%, with the chart type of histogram and grades 0-5; graph 620 displays selecting a toxicity of dysphagia, an organ at risk as larynx edema, and a volume of 30%, with the chart type of histogram and grades 0-5.

The graphical tool shown in FIG. 6 may also be useful when comparing dosimetric variations in treatments between institutions. For example, navigating such data may help understand inter-institutional differences in plans and diagnosing causes of varying levels of toxicity in different practices.

Treatment Plan Quality

The complex geometrical relationship between critical anatomy and the targeted tissues is predictive of the ability to spare the critical anatomy from radiation damage. The outcome may be a physical dose to a particular part of the patient, and the inputs are shape relationships. The ability to spare OARs using intensity-modulated radiotherapy (IMRT) depends on the geometric relationship of each OAR to the target volume. Where the target volume is related to but is not necessarily the tumor size. For example, OARs that are very close to the target are much harder to spare than those far away. Overlap volume histograms (OVH) may describe the complex relationship between the OAR and targets and are stored in the database. An OVH describes how far away a given percent of the OAR's volume is from a target. A medical practitioner may be able to quickly determine an expected dose for a new patient by querying the lowest dose achieved for all patients whose percent volume of the OAR is closer to the target than the new patient's OAR.

Figure 7:
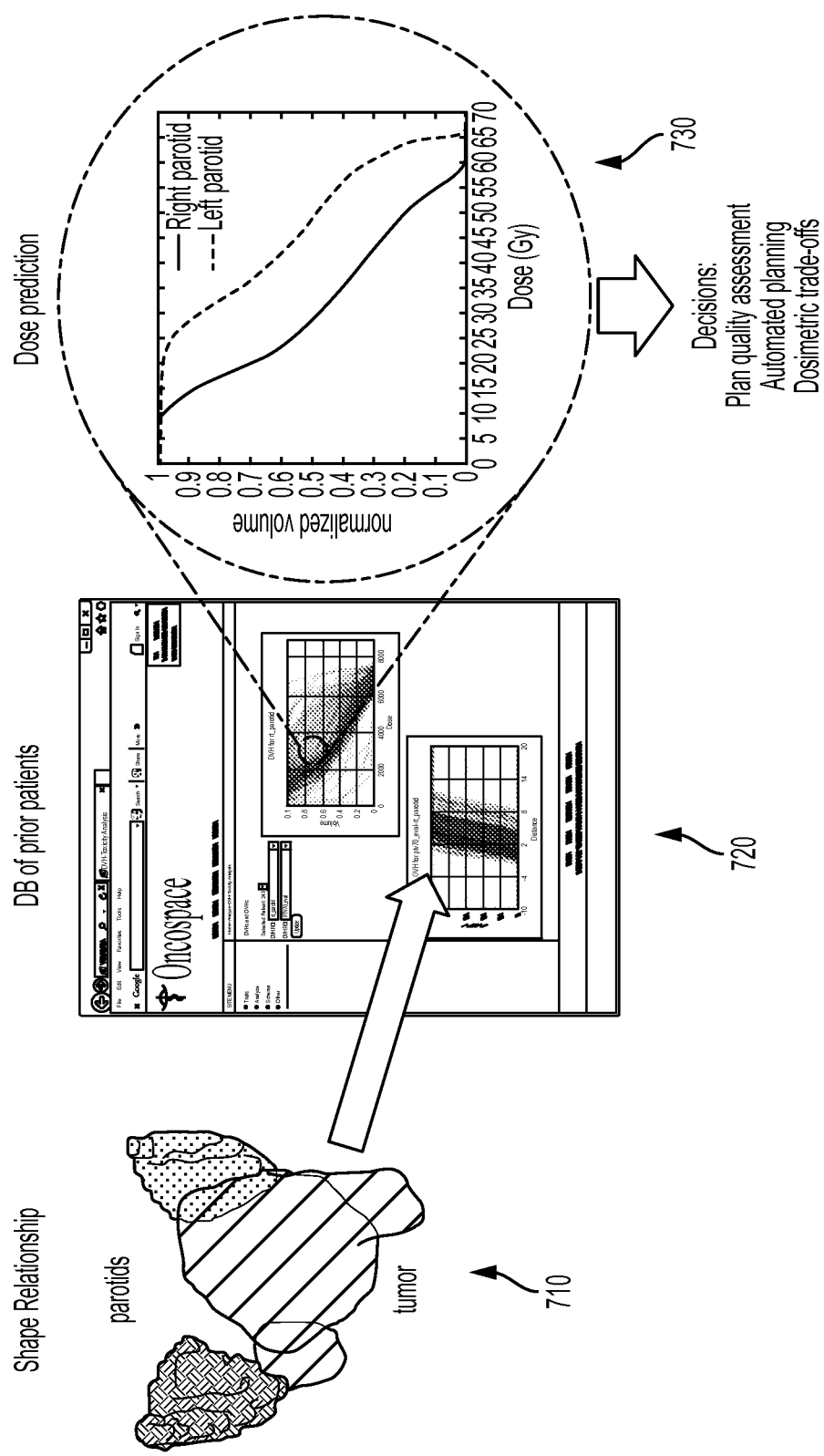
FIG. 7 displays an example query result showing dose prediction based on the tumor and the distance to one or more organs at risk.

FIG. 7 displays the OVH and DVH data. To predict the entire treatment plan quality, the query may be repeated for all OAR's and for any percent volume of each OAR. This model may be used to compare plan quality and to automate the IMRT planning process. In particular, shape relationship 710 illustrates a sample tumor and the right and left parotids. Webpage 720 illustrates a sample webpage where a query can be entered and the results displayed based on the database of patient medical information. Dose prediction 730 shows an enhanced view of doses for the left and right parotid based on distance and target volume. For example, this query searches the database for all patients and finds the best dose for that target area.

Webpage 720 provides input of the following, for a selected OAR and percent volume, find the lowest dose achieved from all patients whose percent volume is closer to the selected target. This question may form the basis for geometry based IMRT plan automation and quality control where dosimetric sparing may be predicted from the database of prior patients as input to the IMRT planning process for a new patient.

The OVH may also assist with inter-institutional comparisons of plan quality. By comparing patients with similar OVH's at the different institutions, it becomes possible to compare the efficacy of different planning techniques in meeting or exceeding normal tissue dose constraints. As plan quality may directly influence patient outcomes both in terms of local tumor control and normal tissue toxicities, the OVH can be used to "normalize" variations in plan quality to improve the consistency of multi-institutional studies.

Through the use of regions of interest 204 table, shape descriptor table, and shape relationship table, it may be possible search on similar shaped tumors. Shape relationship table is a m:n table that provides for a data between one shape and another shape. The shape descriptor table provide data to characterize features of tumors (e.g., volume, concavity, etc.).

OVH may also assist with inter-institutional comparisons of plan quality. By comparing patients with similar OVH's at different institutions, variability due to differences in patient shape relationships may be reduced. This may assist in isolating the evaluation to planning techniques and physician variability in clinical trade-offs.

Dose-Volume Analysis of Normal Tissue Complication Probability

An embodiment may be applied to the prediction of radiation-induced toxicities and treatment outcomes. Although shape relationships and dose may be a subset of the parameters associated with toxicities and outcomes, models may be built that focus on predicting toxicities and outcomes experienced by patients. Data may be mined to find the predictive dosimetric factors from dose volume histograms of OARs and the clinical outcome of the patients.

In one embodiment, a general purpose data-mining framework for large-scale analysis of dose-toxicity relationships may be established to explore the variety and volume of treatment planning data and clinical outcomes available in a database. This may involve, for example, a two-level hierarchical model: a top-level data-mining function for extracting and iterating over combinations of risk structures and outcomes, and a subroutine for executing specific dose-outcome analyses.

The top-level function may extract OARs and outcomes that have been recorded in a database for at least 100 patients. Combination structures may be automatically created from paired OARs based on database naming conventions. For example, the differential DVH curves (e.g., absolute volume, absolute dose, and matching histogram bins) for "l_parotid" and "r_parotid" may be summed to generate a new differential DVH curve for the "combined_parotids". For QoL and toxicity assessment, the query may return the severity of outcomes and the relative date of assessment, defined as the number of days after the first radiotherapy fraction. This allows outcome data to be analyzed as a function of time or over finite time intervals relative to the beginning of treatment. For each combination of OAR and outcome, patients that do not have both OAR and outcome records may be excluded from analysis.

Because this data mining algorithm may be intended to explore such a large number of OAR-outcome combinations, analysis that is efficient to implement for each combination may be required. However, given the depth of dose data in the database, a comprehensive model capable of exploring detailed dose-volume interactions may be desired. While several existing models may be suitable to this end, a logistic regression model may be implemented. A logistic regression model may enable one or more significant dose-volume planning objectives to be explored, as single points in dose-volume space may not adequately predict the risk of radiation-induced toxicities.

Figure 8:
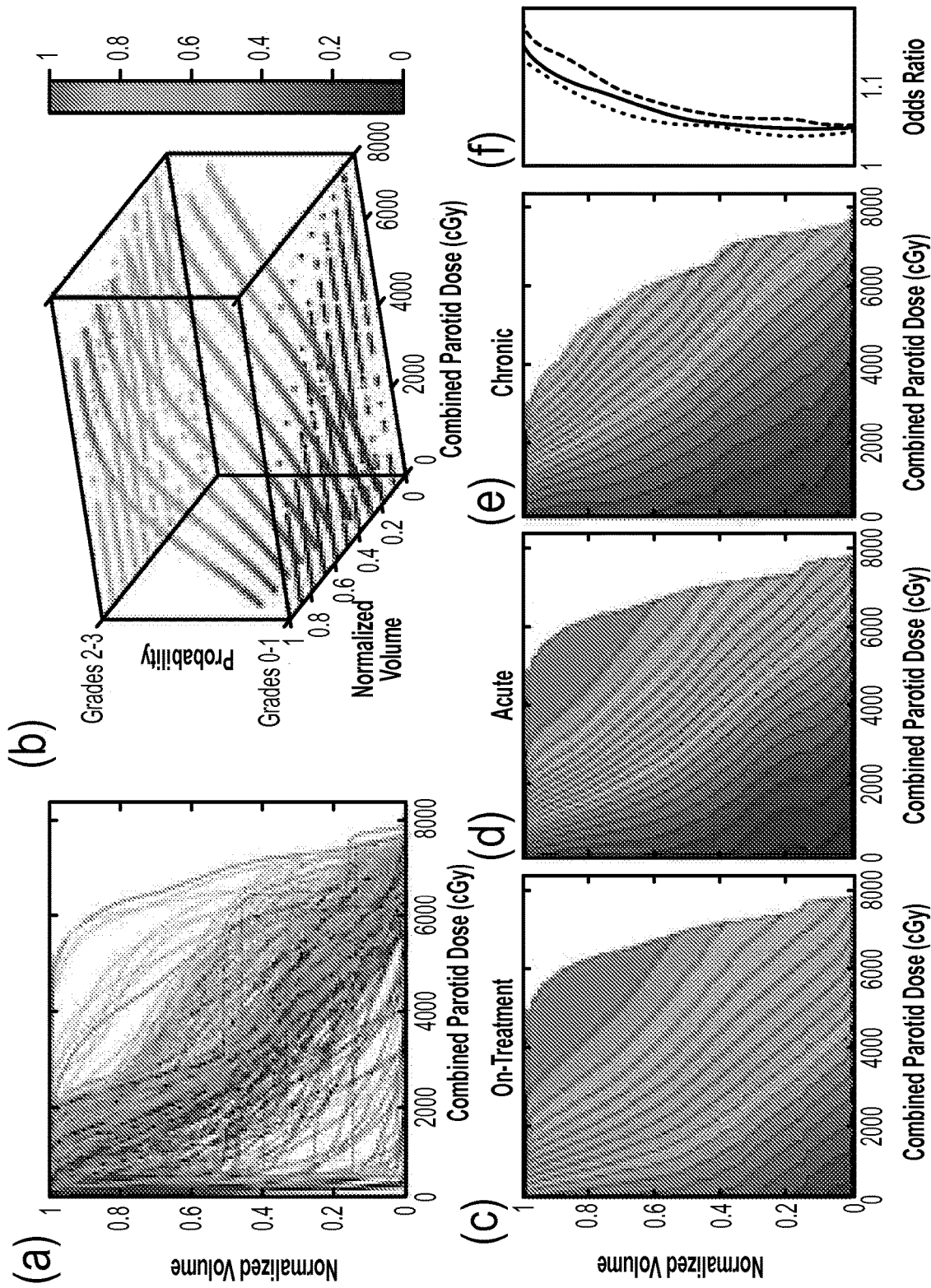
FIG. 8 depicts example logistic regression curves.

FIG. 8 depicts example logistic regression curves. For example, FIG. 8 (a) dose-volume histogram (DVH) curves; (b) logistic regression curves between low-grade and high-grade toxicity groups at normalized volume; (c)-(e) logistic regression curves demonstrating the prevalence of high-grade xerostomia during treatment, acutely and chronically; and (f) odds ratios for on-treatment (solid), acute (dashed), and chronic (dotted) logistic models.

In FIG. 8(*b*), the logistic regression curves are shown for analyses from 10% to 90% normalized volume, in 10% increments. By repeating the logistic regression analysis at a finer volume resolution, the probability of a given outcome may be visualized as a heat map (e.g., FIG. 8(*c*)-(*e*)), with high-gradient regions indicating a highly discriminating region in dose-volume space with respect to the given outcome.

To characterize the strength of the relationship between each combination of OAR and outcome, it may be possible to derive an odds ratio directly from the logistic regression fitting parameters. A larger OR indicates that the probability of an outcome may be more strongly associated with an increase in OAR dose. The maximum OR and associated volume level for each ROI-outcome combination may therefore be used to identify the strongest dose-outcome relationships in the database.

In one study, from a total of 57 OAR and 97 outcomes, Table 1 summarizes the notable dose-toxicity relationships extracted from a database. Many of these relationships in this study agree with literature-based recommendations. For example, with respect to xerostomia, the recommended mean dose to the combined parotid glands is approximately 25 Gy. In the current study, a dose of 27.5 Gy to 50% of the combined parotids resulted in a 50% probability of ≥G2 xerostomia. It is also recommended that high doses to the ipsilateral parotid should be counteracted by doses less than 20 Gy to the contralateral parotid. The data demonstrates that the odds ratio for xerostomia increases with larger normalized volume thresholds. This supports the conclusion that the "low-dose bath" delivered to large volumes (>80%) of the combined parotid tissue may have a stronger influence on xerostomia outcomes than mean dose.

Table 1 describes a summary of notable On-Treatment, Acute and Late dose-outcome relationships identified by having a high odds ratio. These relationships are not presented as clinical recommendations but serve to summarize the rate of common toxicities for patients treated at our institution. Irradiated structures may not have a direct influence on corresponding outcomes, but the dose to neighboring risk structures appears to have a similar influence on outcomes.

TABLE 1

| Outcome | Grade | Organ at Risk | Total Patients | Patient with Outcome | Normalized Volume Threshold | Odds Ratio | p-value |
|---|---|---|---|---|---|---|---|
| ON-TREATMENT | | | | | | | |
| Dehydration | ≥2 | Mandible | 409 | 71 (17%) | 1.00 | 1.075 | <0.001 |
| Dehydration | ≥2 | Masticatory muscles | 217 | 47 (22%) | 1.00 | 1.080 | <0.001 |
| Dehydration | ≥2 | Oral mucosa | 272 | 59 (22%) | 0.00 | 1.172 | <0.001 |
| Dehydration | ≥2 | Parotid glands | 385 | 71 (18%) | 1.00 | 1.143 | <0.001 |
| Dysgeusia | ≥2 | Mandible | 428 | 338 (79%) | 1.00 | 1.137 | <0.001 |
| Dysgeusia | ≥2 | Masticatory muscles | 236 | 201 (85%) | 1.00 | 1.179 | <0.001 |
| Dysgeusia | ≥2 | Parotid glands | 404 | 319 (79%) | 1.00 | 1.189 | <0.001 |
| Esophagitis | ≥2 | Esophagus | 248 | 84 (34%) | 0.04 | 1.052 | <0.001 |
| Esophagitis | ≥2 | Larynx | 91 | 38 (42%) | 0.06 | 1.088 | 0.006 |
| Esophagitis | ≥2 | Thyroid | 243 | 65 (27%) | 0.48 | 1.091 | <0.001 |
| Mucositis | ≥3 | Mandible | 431 | 242 (56%) | 1.00 | 1.074 | <0.001 |
| Mucositis | ≥3 | Masticatory muscles | 237 | 136 (57%) | 0.00 | 1.103 | <0.001 |
| Mucositis | ≥3 | Oral mucosa | 295 | 159 (54%) | 0.99 | 1.051 | <0.001 |
| Nausea | ≥2 | Brainstem | 452 | 175 (39%) | 0.01 | 1.052 | <0.001 |
| Nausea | ≥2 | Mandible | 432 | 167 (39%) | 1.00 | 1.095 | <0.001 |
| Nausea | ≥2 | Masticatory muscles | 238 | 108 (45%) | 1.00 | 1.105 | <0.001 |
| Nausea | ≥2 | Oral mucosa | 296 | 134 (45%) | 0.00 | 1.082 | <0.001 |
| Nausea | ≥2 | Parotid glands | 407 | 163 (40%) | 1.00 | 1.158 | <0.001 |
| Nausea | ≥2 | Spinal cord | 468 | 176 (38%) | 0.52 | 1.070 | <0.001 |
| Voice changes | ≥2 | Larynx | 170 | 62 (36%) | 0.09 | 1.091 | <0.001 |
| Xerostomia | ≥2 | Mandible | 431 | 273 (63%) | 1.00 | 1.120 | <0.001 |
| Xerostomia | ≥2 | Masticatory muscles | 237 | 168 (71%) | 1.00 | 1.122 | <0.001 |
| Xerostomia | ≥2 | Oral mucosa | 295 | 219 (74%) | 0.00 | 1.069 | <0.001 |
| Xerostomia | ≥2 | Parotid glands | 406 | 270 (67%) | 1.00 | 1.173 | <0.001 |
| ACUTE (0-3 months) | | | | | | | |
| Dysgeusia | ≥2 | Mandible | 346 | 141 (41%) | 1.00 | 1.069 | <0.001 |
| Dysgeusia | ≥2 | Parotid glands | 325 | 140 (43%) | 1.00 | 1.110 | <0.001 |
| Dysphagia | ≥2 | Constrictor muscles | 186 | 35 (19%) | 0.03 | 1.105 | 0.012 |
| Dysphagia | ≥2 | Larynx | 134 | 31 (23%) | 0.03 | 1.160 | 0.001 |
| Voice changes | ≥1 | Larynx | 136 | 71 (52%) | 0.03 | 1.120 | <0.001 |
| Xerostomia | ≥2 | Mandible | 349 | 164 (47%) | 1.00 | 1.108 | <0.001 |
| Xerostomia | ≥2 | Masticatory muscles | 186 | 100 (54%) | 0.00 | 1.074 | 0.004 |
| Xerostomia | ≥2 | Oral mucosa | 230 | 126 (55%) | 0.00 | 1.108 | <0.001 |
| Xerostomia | ≥2 | Parotid glands | 328 | 168 (51%) | 1.00 | 1.166 | <0.001 |
| LATE (3-12 mo) | | | | | | | |
| Dental caries | ≥1 | Oral mucosa | 212 | 35 (17%) | 0.00 | 1.099 | 0.047 |
| Dental caries | ≥1 | Parotid glands | 296 | 36 (12%) | 1.00 | 1.137 | 0.001 |
| Dysgeusia | ≥2 | Mandible | 302 | 60 (20%) | 1.00 | 1.064 | 0.002 |
| Dysgeusia | ≥2 | Parotid glands | 296 | 61 (21%) | 0.99 | 1.082 | 0.002 |
| Dysphagia | ≥1 | Constrictor muscles | 176 | 77 (44%) | 0.00 | 1.105 | 0.003 |
| Dysphagia | ≥1 | Larynx | 133 | 68 (51%) | 0.04 | 1.061 | 0.014 |
| Hearing changes | ≥2 | Ear canals | 169 | 37 (22%) | 0.97 | 1.058 | <0.001 |
| Hearing changes | ≥2 | Masticatory muscles | 177 | 46 (26%) | 1.00 | 1.069 | 0.006 |
| Hearing changes | ≥2 | Temporomandibular | 172 | 41 (24%) | 0.99 | 1.059 | <0.001 |
| Trismus | ≥1 | Mandible | 302 | 80 (26%) | 0.08 | 1.060 | 0.001 |
| Trismus | ≥1 | Masticatory muscles | 178 | 50 (28%) | 0.15 | 1.063 | 0.005 |
| Trismus | ≥1 | Parotid glands | 299 | 72 (24%) | 1.00 | 1.095 | 0.003 |
| Voice changes | ≥1 | Larynx | 133 | 67 (50%) | 0.00 | 1.251 | <0.001 |
| Xerostomia | ≥2 | Mandible | 303 | 123 (41%) | 1.00 | 1.092 | <0.001 |
| Xerostomia | ≥2 | Masticatory muscles | 180 | 89 (49%) | 1.00 | 1.065 | 0.007 |
| Xerostomia | ≥2 | Oral mucosa | 216 | 101 (47%) | 0.00 | 1.086 | 0.002 |
| Xerostomia | ≥2 | Parotid glands | 300 | 128 (43%) | 1.00 | 1.153 | <0.001 |

For dysphagia, several studies have reported a high degree of intercorrelation between mean dose and partial-volume dose models for the larynx and pharyngeal constrictor muscles. Increasing odds ratio for decreasing larynx and pharyngeal constrictor volumes may be observed from the data, with a maximum OR occurring at 3% volume for both structures. Therefore, a high dose model may have greater predictive power than either mean or median dose models. This illustrates the ability of the current data-mining paradigm to explore the nature of thousands of dose-outcome relationships.

In one embodiment, an analytic pipeline may be created that transforms medical data (e.g., data in Oncospace) into a format suitable for creating multiple ad hoc NTCP prediction models. This may include the incorporation of spatial dose information and patient-specific factors to improve upon existing models. By creating a data science platform for robust, data-driven NTCP models, it may be possible to create safer, personalized treatment plans based on the experience gained from treating prior patients.

Machine learning models such as linear regression (LR), random forest (RF), naïve Bayes (NB), bagged LR (BLR), and NB (BNB) may incorporate spatial distribution of dose for, for example, voice dysfunction and xerostomia (dry mouth) due to irradiation of the larynx and parotid glands, respectively. Features may be selected using information gain; and models may be evaluated using the receiver operating characteristic area under the curve (AUC). A real-world embodiment showed strong outperformance of the spatial models to the standard Lyman-Kutcher Burman models of NTCP for voice dysfunction which supports a relationship between the complication and dose placement.

Spatial features for modeling voice dysfunction may be created from a single region (e.g., the larynx); spatial features for modeling xerostomia, for example, may be created from the individual parotids. Organ regions may be manually contoured in the course of the clinical workflow. Therefore, the actual shape and location of regions may vary substantially. Spatial features may be created that are sufficiently specific as to be informative and still general enough to avoid capturing non-relevant variation. Spatial feature selection may be a critical component to utilizing the learning models and they must relate to the critical function and radio-sensitivity of the anatomy, but also must be consistent and correlated across patients.

In one embodiment, a set of features may be created using spatial dose visualizations. Each region's spatial dimensions may be divided into fifths, for example, using the maximum and minimum values for the dimension; yielding 15 sub-regions per region. The percentage of the total dose within the band delivered to each sub-region may be calculated. These values may be referred as "dose grid distributions" for a band, on a region's ith dimension's jth bin. This process created, for example, 75 features per region.

In one embodiment, for example, a machine learning method may find that a high mandible dose is predictive of xerostomia. However, physiologically the mandible is not responsible for salivary function. Yet, a high mandible dose is an indication that there is also a high parotid dose as the variables are correlated through the dose distribution. So, in this case the mandible dose is correlated with xerostomia but not the cause.

Toxicity Trend Review

Toxicities in RT may be acute and may occur during treatment and subside after treatment or the toxicities may have chronic late effects that are permanent and impact patients' long term quality of life. The scoring of toxicities during on-treatment visits and in follow up for all patients can provide for the capture, storage, monitoring and analyzing of the results of care.

Figure 9:
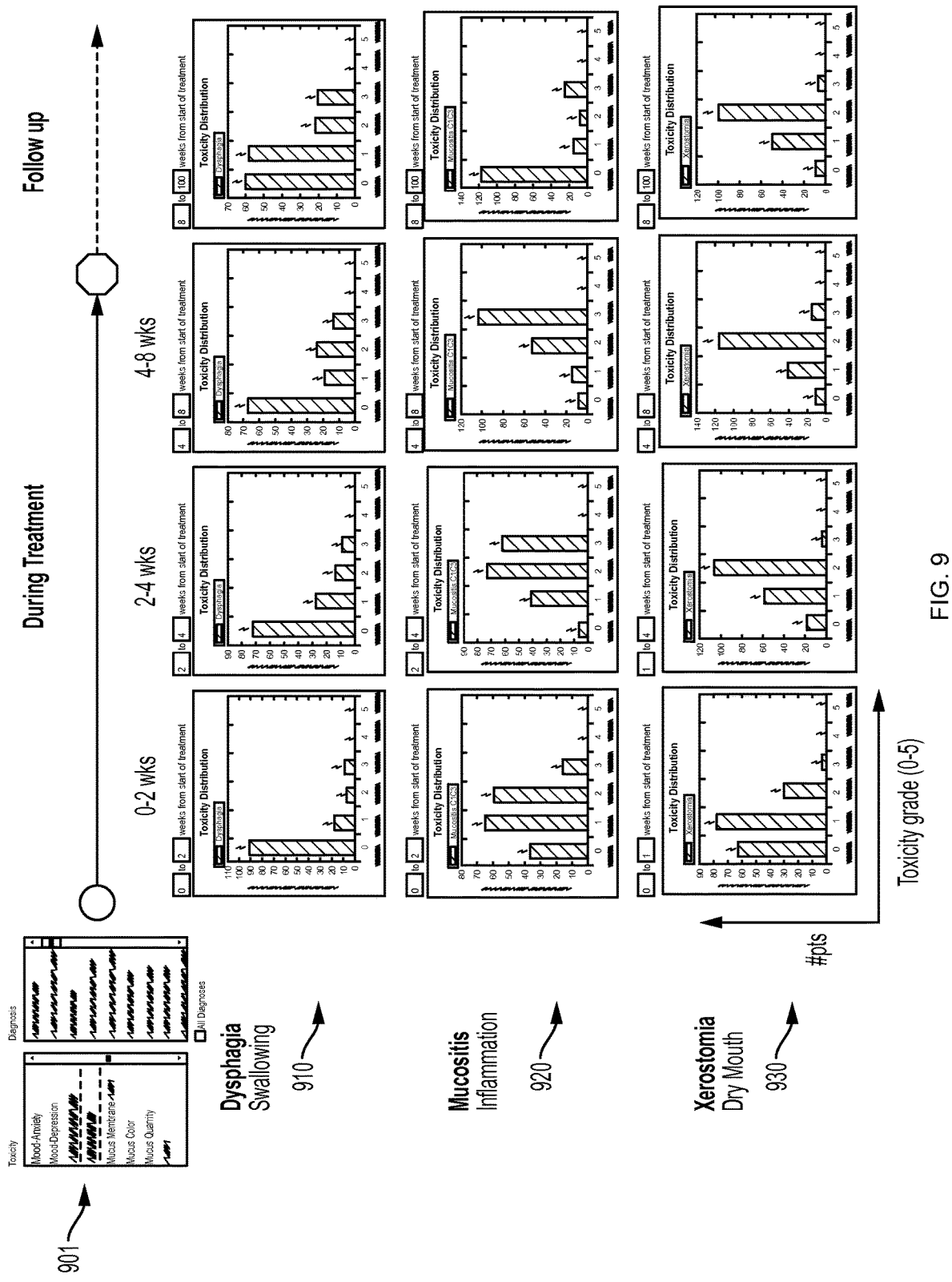
FIG. 9 displays example query result showing toxicities and when the occurrences of the toxicities previously occurred.

FIG. 9 displays webpage 901 that allows input of a particular group of diagnoses and a particular toxicity. In one embodiment, histograms of the maximum grade experienced by the patients within the specified time period from the start of treatment may be plotted. For example, as shown in the graphs of FIG. 9, for head and neck diagnoses, graph 910 shows that dysphagia tends to occur late in the treatment and into follow up, whereas graph 920 shows that mucositis can occur early in treatment and then resolves after the radiation is completed, and graph 930 shows that xerostomia can develop towards the end of treatment and can remain permanent. Graphs, such as graphs 910, 920, and 930, may be used for patient education to discuss what may be expected during their treatment. In addition, graphs, such as graphs 910, 920, and 930, may be used to detect when a patient may be an outlier (e.g., deviates from a typical patient undergoing the same treatment) and may need additional intervention to help control a toxicity. Graphs, such as graphs 910, 920, and 930, may also allow the care team to investigate their own practice, to understand where improvements may be needed, and to assist in understanding a particular patient.

Webpage 901 provides a medical practitioner with the ability to query a selected diagnoses and toxicity and to display on graphs, such as graphs 910, 920, and 930, the aggregate trend in toxicity from start of treatment through several year follow-up. In so doing, an embodiment may determine if the current patient is an outlier or experiencing normal side effects Webpage 901 shows an interactive display where users may multi-select diagnosis and a toxicity and, through graphs, such as graphs 910, 920, and 930, see a distribution of the number of patients in each time period experiencing a particular maximum grade of the specified toxicity. For example, in graph 910, the onset of dysphagia occurs after treatment for many patients, in graph 920, mucositis progressively increases during treatment but heals in the longer term, and in graph 930, xerostomia starts towards the middle/end of treatment and remains permanent.

Inter-institutional comparisons of toxicity trends may also be made. Variability in trends may be due to varying techniques in symptom management or variability in radiation dose delivery. By having data readily accessible, such comparisons can be made interactively thereby assisting the community in improving care.

As clinical practice evolves, treatment methods continually improve, and in turn improvement in treatment outcomes result. Clinical trials have difficulties in keeping up with advancements in care as they take years for results to be acquired, analyzed and communicated. An advantage of using clinical data is that with each new patient the system may learn and as clinical practice evolves care may be improved.

Government regulations and institutional restrictions impede the ability to share and access data. An embodiment (e.g., the Oncospace system) may be designed to protect PHI on patients, but there may remain restrictions on what data individual institutions and physicians are willing to share as there is research value and also performance measures that institutions would like to protect. Data sharing may require communal participation agreements that clearly define how and what data can be shared, and the type of analysis that is allowed. An embodiment herein may easily adapt to such requirements, as access and analysis can be restricted through the website based portal and/or database security measures.

Embodiments described herein present a model of aggregating clinical data from a medical practice on a continual basis. An embodiment may integrate data collection into the clinical workflow, providing a system to house and aggregate the data in a protected manner, and providing web-based tools to navigate and recall past experience to assist in improving the safety and quality of care for new patients. Allowing data sharing across multiple institutions may represent a data driven model for advancing the practice of, for example, RT. Clinical questions may be addressed to improve clinical care. Multiple institutions sharing data to support clinical decisions may improve the ability to advance care based on data collected on routinely treated patients outside of clinical trials as well as from those on formal clinical studies. Accordingly, individualization of care with real-time analysis of similar patients' outcomes and complications may be possible. Furthermore, the example comprehensive database described herein may enable prospective quality analysis and quantitative prediction of treatment outcomes and toxicities with a level of statistical confidence which was previously not available. In addition to improving care, cost-effectiveness of treatment options may be explored and compared to outcome and quality of life measures.

Figure 10:
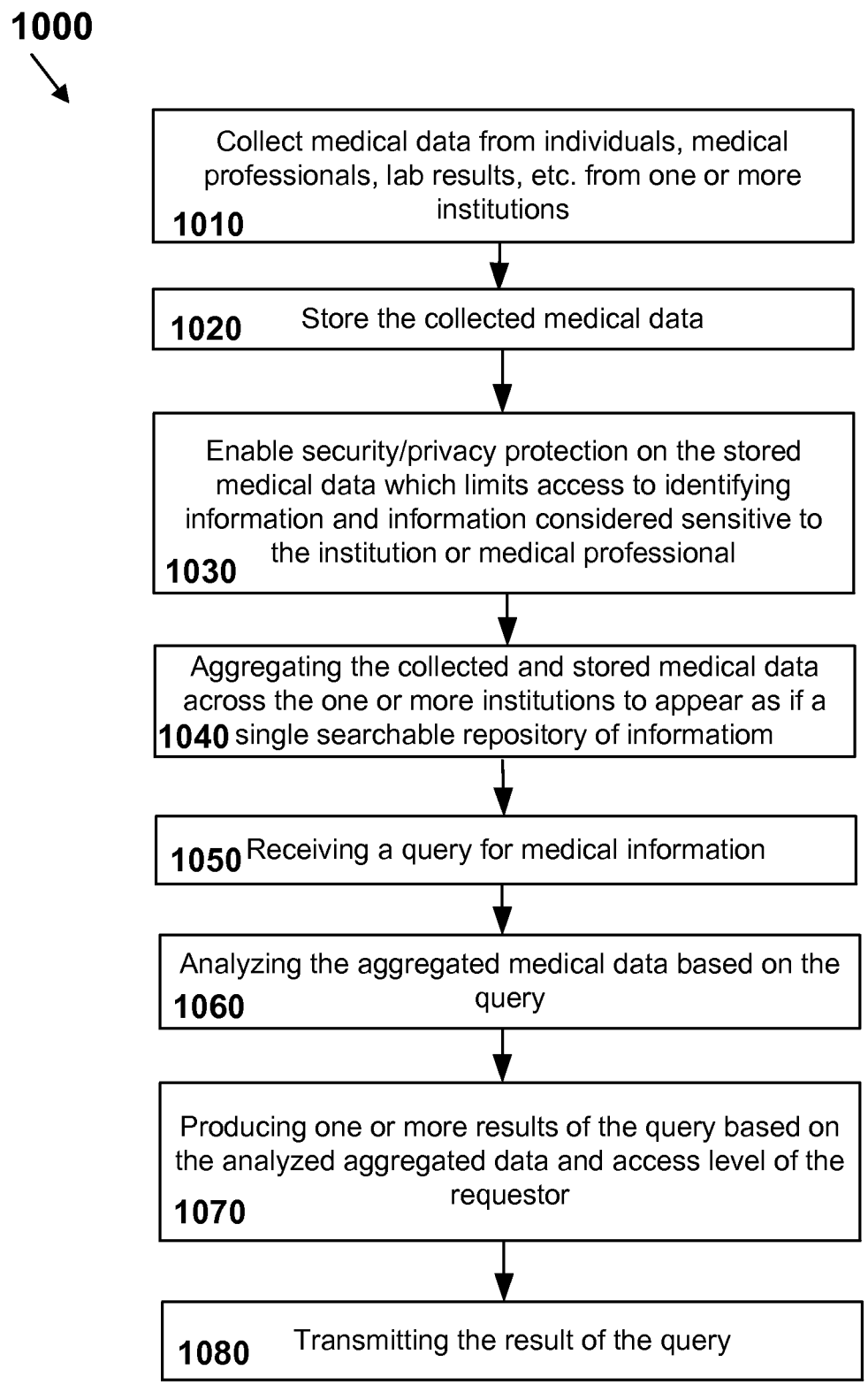
FIG. 10 depicts an example medical data analysis and sharing workflow.

FIG. 10 provides an example workflow for analyzing and disseminating medical information that may be used in an example embodiment of the present invention. The workflow may be performed using one or more computers connected to one or more computer systems. Flow may begin in 1010.

In 1010, medical data may be collected from individuals, medical professionals, lab results, or from other sources of medical information. The medical data may pertain to patients who are being treated at one or more institutions (e.g., universities, hospitals, clinics, research facilities, etc.). The medical information may be acquired through the use of mobile tablet devices, desktop computers, or automatically through automated lab result systems. Medical data may include, for example, personal identifiable information (e.g., information that may identify the patient), diagnostic information, prognosis information, toxicology results, a disease name, a staging of the disease, patient geometries, target information, vital signs, lab values, medications, chemotherapy prescriptions, radiation treatment prescriptions, radiation therapy plans, family history, social history, medical history, past and current surgical procedures, assessment information, tumor features, a radiation summary, organ dose summaries, patient representations, regions of interest, radiotherapy session information, organs at risk, spatial relationships of the one or more organs at risk, dose distributions, dose volume histograms, toxicity information, disease progression information, and/or demographic information. From 1010, flow may move to 1020.

In 1020, the collected medical data may be stored in a storage repository such as a relational database. The data stored in the relational database, for example, may be stored to facilitate fast retrieval for queried medical information for patients with a similar disease or prognosis. The medical data may be stored in tables such as those described in FIG. 1. From 1020, flow may move to 1030.

In 1030, the medical data may be protected from unauthorized access under both required regulation and policies unique to the institutions. For example, data that could uniquely identify an individual or patient (e.g., name, address, etc.) may be restricted to only authorized individuals or may be removed from the database (e.g., a limited data set in compliance with HIPAA regulations). Additionally, some medical information may be restricted based on the institution, allowing some institutions more access to information than other institutions. For example, an institution may be hoping to publish the results of a particular treatment and does not wish a potentially rival institution from obtaining this knowledge prior to publication, yet may still wish to share some medical information. Some institutions may have policies that may prohibit making money on patient data (e.g., no fee for service). Other institutions may not wish to provide information on toxicity rates. In some situations, some data may be provided so that institutions can compare data in the aggregate but not to compare data between specific institutions. Tools may be built to implement the privacy policies of the institutions but still enable aggregate sharing of data. The tools may also be built to enable a limited time or special arrangement of data sharing that may be typically against the institution's policy. Privacy may be restricted using database security or website based security. From 1030, flow may move to 1040.

In 1040, the medical information databases of the one or more institutions may be aggregated to appear as one repository of searchable medical information. From 1040, flow may move to 1050.

In 1050, a query may be received requesting medical information. The query may be created from a web based form that provides, for example, a set of selectable options that allow a medical professional to search the aggregated data for medical information. Queries may include, for example, (a) for patients with a selected diagnosis and disease histology, what is the distribution of dose-fractionation prescribed? (b) For a selected toxicity and organ at risk, display the dose volume histograms and colorize them by the maximum toxicity grade of the patient. For a specified organ at risk volume percentage, graph the mean dose received for each toxicity grade. (c) For a selected organ at risk and percent volume, find the lowest dose achieved from all patients whose percent volume is closer to the selected target volume. (d) For a selected diagnosis, toxicity and treatment, display the aggregate trend in toxicity from start of treatment (acute) through several year follow-up (late). From 1050, flow may move to 1060.

In 1060, the aggregated medical data may be analyzed based on the received query. From 1060, flow may move to 1070.

In 1070, one or more results of the received query may be produced based on the aggregated data. The results may include tables, charts, alerts, and/or graphs representing a possible answer to the query. From 1070, flow may move to 1080.

In 1080, the results of the query may be transmitted to the requestor of the query.

In one embodiment, a result may include information on patients with a similar diagnosis, pathology, and/or treatment site and an accompanying alert if the treated patient treatment information deviates from the treatment information for similar patients.

Another embodiment may include information on patient prescriptions and an accompanying alert if the patient prescription information deviates from the patient prescription information for patients with the similar diagnosis, pathology, and treatment site.

Data Integrity

In another embodiment, the data stored in the database may be checked for data integrity and completeness. A component may search the database for data values that are missing and/or inconsistent with other recorded data values. For example, doses may be inadvertently entered that may be detected as incorrect based on known dosing. Once a data value has been identified, the value may be flagged to allow an operator to examine the data value and determine if it is incorrect. Bad data may be detected and removed to ensure quality and consistency to the data.

Computer System

Figure 11:
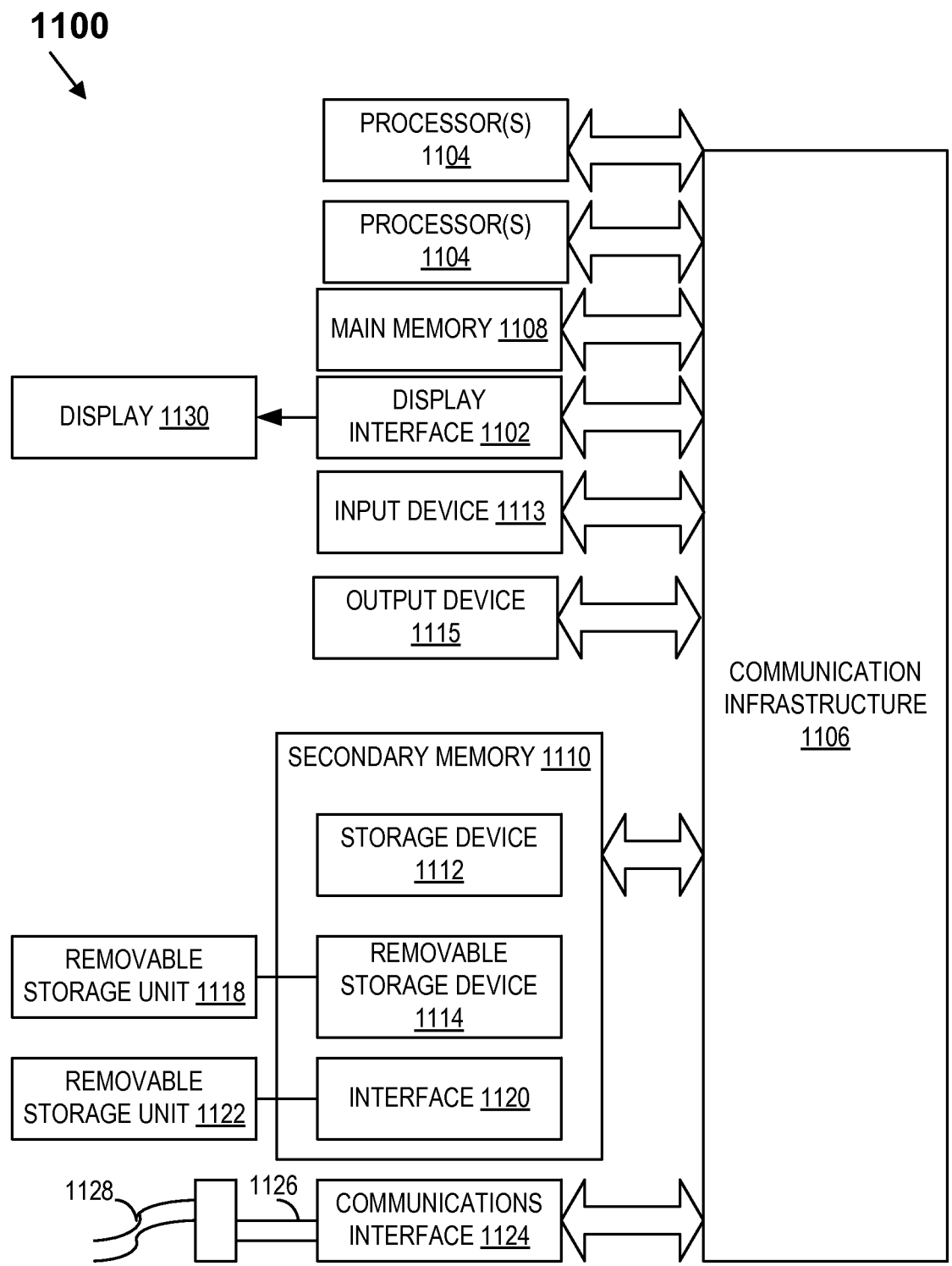
FIG. 11 depicts an illustrative embodiment of a computer for performing the methods and building the systems described herein.

FIG. 11 depicts an illustrative computer system that may be used in implementing an illustrative embodiment of the present invention. Specifically, FIG. 11 depicts an illustrative embodiment of a computer system 1100 that may be used in computing devices such as, e.g., but not limited to, mobile phones, smart phones, tablets, standalone computers, client and/or server devices. FIG. 11 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In one illustrative embodiment, the invention may be directed toward one or more computer systems capable of carrying out the functionality described herein. An example of a computer system 1100 is shown in FIG. 11, depicting an illustrative embodiment of a block diagram of an illustrative computer system useful for implementing the present invention. Specifically, FIG. 11 illustrates an example computer 1100, which in an illustrative embodiment may be, e.g., (but not limited to) a personal computer (PC) system running an operating system such as, e.g., (but not limited to) MICROSOFT® WINDOWS® XP/Vista/Windows 7/Windows 8 etc. available from MICROSOFT® Corporation of Redmond, Wash., U.S.A. or an Apple computer executing MAC® OS or iOS from Apple® of Cupertine, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. Other components of the invention, such as, e.g., (but not limited to) a computing device, a communications device, a telephone, a personal digital assistant (PDA), a tablet, an iPad, a Surface, an Android device, an iPhone, a 3G wireless device, an LTE wireless device, a wireless device, a personal computer (PC), a handheld PC, a laptop computer, a smart phone, a mobile device, a netbook, a handheld device, a portable device, an interactive television device (iTV), a digital video recorder (DVR), client workstations, thin clients, thick clients, fat clients, proxy servers, network communication servers, remote access devices, client computers, server computers, peer-to-peer devices, routers, web servers, data, media, audio, video, telephony or streaming technology servers, etc., may also be implemented using a computer such as that shown in FIG. 11. In an illustrative embodiment, services may be provided on demand using, e.g., an interactive television device (iTV), a video on demand system (VOD), via a digital video recorder (DVR), and/or other on demand viewing system. Computer system 1100 may be used to implement the invention as described herein and depicted at least in FIGS. 1-10.

The computer system 1100 may include one or more processors, such as, e.g., but not limited to, processor(s) 1104. The processor(s) 1104 may be connected to a communication infrastructure 1106 (e.g., but not limited to, a communications bus, cross-over bar, interconnect, or network, etc.). Processor 1104 may include any type of processor, microprocessor, or processing logic that may interpret and execute instructions (e.g., for example, a field programmable gate array (FPGA)). Processor 1104 may comprise a single device (e.g., for example, a single core) and/or a group of devices (e.g., multi-core). The processor 1104 may include logic configured to execute computer-executable instructions configured to implement one or more embodiments. The instructions may reside in main memory 1108 or secondary memory 1110. Processors 1104 may also include multiple independent cores, such as a dual-core processor or a multi-core processor. Processors 1104 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 1100 may include a display interface 1102 that may forward, e.g., but not limited to, graphics, text, and other data, etc., from the communication infrastructure 1106 (or from a frame buffer, etc., not shown) for display on the display unit 1130. The display unit 1130 may be, for example, a television, a computer monitor, or a mobile phone screen. The output may also be provided as sound through, for example, a speaker.

The computer system 1100 may also include, e.g., but is not limited to, a main memory 1108, random access memory (RAM), and a secondary memory 1110, etc. Main memory 1108, random access memory (RAM), and a secondary memory 1110, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory 1110 may include, for example, (but is not limited to) a hard disk drive 1112 and/or a removable storage drive 1114, representing a floppy diskette drive, a magnetic tape drive, an optical disk drive, a compact disk drive CD-ROM, flash memory, etc. The removable storage drive 1114 may, e.g., but is not limited to, read from and/or write to a removable storage unit 1118 in a well-known manner. Removable storage unit 1118, also called a program storage device or a computer program product, may represent, e.g., but is not limited to, a floppy disk, magnetic tape, optical disk, compact disk, flash memory, etc. which may be read from and written to removable storage drive 1114. As will be appreciated, the removable storage unit 1118 may include a computer usable storage medium having stored therein computer software and/or data.

In alternative illustrative embodiments, secondary memory 1110 may include other similar devices for allowing computer programs or other instructions to be loaded into computer system 1100. Such devices may include, for example, a removable storage unit 1122 and an interface 1120. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1122 and interfaces 1120, which may allow software and data to be transferred from the removable storage unit 1122 to computer system 1100.

Computer 1100 may also include an input device 1113 may include any mechanism or combination of mechanisms that may permit information to be input into computer system 1100 from, e.g., a user. Input device 1113 may include logic configured to receive information for computer system 1100 from, e.g. a user. Examples of input device 1113 may include, e.g., but not limited to, a mouse, pen-based pointing device, or other pointing device such as a digitizer, a touch sensitive display device, and/or a keyboard or other data entry device (none of which are labeled). Other input devices 1113 may include, e.g., but not limited to, a biometric input device, a video source, an audio source, a microphone, a web cam, a video camera, and/or other camera.

Computer 1100 may also include output devices 1115 which may include any mechanism or combination of mechanisms that may output information from computer system 1100. Output device 1115 may include logic configured to output information from computer system 1100. Embodiments of output device 1115 may include, e.g., but not limited to, display 1130, and display interface 1102, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. Computer 1100 may include input/output (I/O) devices such as, e.g., (but not limited to) communications interface 1124, cable 1128 and communications path 1126, etc. These devices may include, e.g., but are not limited to, a network interface card and modems (neither are labeled).

Communications interface 1124 may allow software and data to be transferred between computer system 1100 and external devices.

In this document, the terms "computer program medium," "computer readable medium," and "non-transitory computer readable medium" may be used to generally refer to media such as, e.g., but not limited to, removable storage drive 1114, a hard disk installed in hard disk drive 1112, flash memories, removable discs, non-removable discs, etc. In addition, it should be noted that various electromagnetic radiation, such as wireless communication, electrical communication carried over an electrically conductive wire (e.g., but not limited to twisted pair, CATS, etc.) or an optical medium (e.g., but not limited to, optical fiber) and the like may be encoded to carry computer-executable instructions and/or computer data that embodiments of the invention on e.g., a communication network. These computer program products may provide software to computer system 1100. It should be noted that a computer-readable medium that comprises computer-executable instructions for execution in a processor may be configured to store various embodiments of the present invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general purpose device selectively activated or reconfigured by a program stored in the device.

Embodiments may be embodied in many different ways as a software component. For example, it may be a stand-alone software package, or it may be a software package incorporated as a "tool" in a larger software product, such as, for example, a scientific modeling product. It may be downloadable from a network, for example, a website, as a stand-alone product or as an add-in package for installation in an existing software application. It may also be available as a client-server software application, or as a web-enabled software application.

While various embodiments of the present invention have been described above, it should be understood that they have been presented by way of example only, and not limitation. Thus, the breadth and scope of the present invention should not be limited by any of the above-described illustrative embodiments, but should instead be defined only in accordance with the following claims and their equivalents. The various embodiments may be combined.

What is claimed is:

1. A computer-implemented method for analyzing and disseminating medical information from a plurality of medical institutions, the method comprising:

receiving a plurality of patient medical data from the plurality of medical institutions, wherein each of the plurality of medical institutions collects and stores a set of the medical data and controls access to the collected and stored set of medical data;

aggregating the received plurality of patient medical data, wherein each of the plurality of patient medical data comprises patient private health information, wherein access by a third party to said patient medical data is restricted by each medical institution by limiting access to information that the medical institution considers privileged, wherein aggregating the plurality of patient medical data comprises storing the plurality of patient medical data from the plurality of medical institutions in a searchable relational database, the patient medical data being arranged and stored to facilitate fast query, retrieval and analysis, wherein the patient private health information is stored in a separate set of restricted database tables for each medical institution, that are separate and isolated from other, unrestricted database tables in said searchable relational database containing the plurality of patient medical data;

receiving a query for medical information pertaining to a medical condition applicable to a plurality of patients;

searching the other unrestricted database tables in the searchable relational database and extracting the medical information based on the query;

producing a result of the query based on the analyzing of the aggregated medical data, wherein the result of the query does not include any of the patient private health information from the restricted tables; and transmitting the result of the query.

2. The method of claim 1, wherein the patient medical data comprises at least one of: a disease name, a staging of the disease, one or more patient geometries, one or more targets, one or more vital signs, one or more lab values, one or more medications, one or more chemotherapy prescriptions, one or more radiation treatment prescriptions, one or more radiation therapy plans, family history, social history, medical history, one or more surgical procedures, one or more assessments, one or more tumor features, a radiation summary, one or more organ dose summaries, one or more patient representations, one or more regions of interest, radiotherapy session information, one or more organs at risk, one or more spatial relationships of the one or more organs at risk, one or more dose distributions, one or more dose volume histograms, one or more toxicities, one or more diagnoses, one or more disease progressions, or demographics.

3. The method of claim 1, wherein the plurality of patient medical data comprises a first set of medical data that is received from a first medical institution and further comprises a second set of patient medical data that is received from a second medical institution.

4. The method of claim 3, further comprising:
limiting access of the first medical institution to the second set of patient medical data received from the second medical institution.

5. The method of claim 3, wherein only aggregated results of queries are displayed based on data sharing restrictions between the first medical institution and the second medical institution.

6. The method of claim 1, further comprising:
entering the plurality of patient medical data using one or more mobile tablet devices.

7. The method of claim 1, further comprising:
enabling the plurality of patient medical data to be anonymous when the separate set of restricted database tables are removed or when access to the separate set of restricted database tables is restricted.

8. The method of claim 1, further comprising:
receiving patient treatment information, the patient treatment information relating to a patient, the patient treatment information not included in the plurality of patient medical data;
retrieving a plurality of treatment information from the plurality of patient medical data for patients with similar diagnosis, pathology, and treatment site as the patient;
comparing the patient treatment information to the plurality of treatment information; and
transmitting an alert when the patient treatment information deviates from the plurality of treatment information for patients with the similar diagnosis, pathology, and treatment site.

9. The method of claim 1, further comprising:
receiving patient prescription information, the patient prescription information relating to a patient, the patient prescription information not included in the plurality of patient medical data;
retrieving a plurality of patient prescription information from the plurality of patient medical data for patients with similar diagnosis, pathology, and treatment site;
comparing the patient prescription information to the plurality of patient prescription information; and
transmitting an alert when the patient prescription information deviates from the plurality of patient prescription information for patients with the similar diagnosis, pathology, and treatment site.

10. The method of claim 1, wherein the query requests information on a plurality of patient medical information for patients with a similar diagnosis and similar disease histology.

11. The method of claim 1, wherein the query requests information on the distribution of dose-fractionation prescribed for patients with a selected diagnosis and disease histology.

12. The method of claim 1, wherein the query requests displaying dose volume histograms for a selected toxicity and an organ at risk, wherein the dose volume histograms are colorized by a maximum toxicity grade of the patient.

13. The method of claim 12, further comprising displaying a graph of a mean dose received for each toxicity grade for a specified organ at risk volume percentage.

14. The method of claim 1, wherein the query requests a lowest dose achieved from the plurality of patient medical data for all patients whose percent volume is closer to a selected target volume for a selected organ at risk and percent volume.

15. The method of claim 1, wherein the query requests displaying an aggregate trend in toxicity from a start of treatment through multiple years for a selected diagnosis, toxicity, and treatment.

16. The method of claim 1, wherein the query comprises a selection of: toxicity, organ at risk, and percent volume of the organ at risk; and, wherein the result of the query comprises displaying a dose volume histogram color coded by a maximum toxicity grade experienced by a plurality of patients and displaying a plurality of patient distributions of the maximum toxicity grade as a function of dose to the percent volume of the organ at risk.

17. The method of claim 1, wherein the query comprises a request for an expected dose for a new patient by retrieving, from the aggregated medical data, a lowest dose achieved for all patients whose percent volume of an organ at risk is closer to a target than an organ at risk for the new patient.

18. The method of claim 1, wherein the query comprises a request for a particular group of diagnoses and a particular toxicity; and wherein the result comprises a histogram of one or more maximum grades experienced by a plurality of patients within a specified time period from a start of treatment.

19. A system comprising:
one or more mobile tablets for entering medical data at an institution;
one or more storage devices at the institution, the one or more storage devices holding one or more searchable relational databases, the one or more searchable relational databases including one or more unrestricted database tables for storing and organizing the medical data, the one or more searchable relational databases configured to store the medical data to facilitate fast query, retrieval and analysis, the one or more storage devices storing one or more instructions for analyzing and disseminating medical information, wherein patient private health information is stored in a separate restricted database table of said one or more searchable relational databases that is separate and isolated from said one or more unrestricted database tables in said one or more searchable relational database containing the medical data; and
one or more computers, wherein the one or more computers receive the medical data and store the medical data in the one or more searchable relational databases, the one or more computers comprising one or more processors, the one or more processors operable to execute the one or more instructions, the one or more instructions comprising instructions for:
receiving a query for medical information pertaining to a particular medical condition applicable to one or more patients;
retrieving medical information from the one or more storages devices at the institution;
retrieving medical information from a second institution, wherein the second institution controls access to medical data stored at the second institution and wherein the medical information retrieved from the second institution contains no patient private health information;
searching the unrestricted database tables in the one or more searchable relational databases and extracting the medical information based on the query;

producing a result of the query based on the extracted medical information, wherein the result of the query does not include any of the patient private health information from the restricted tables; and transmitting the result of the query.

20. A non-transitory computer-readable medium storing computer-executable instructions, the computer-readable medium storing one or more instructions to:

receive a plurality of patient medical data from a plurality of medical institutions, wherein each of the plurality of medical institutions collects and stores a set of the medical data and controls access to the collected and stored set of medical data;

aggregating the received plurality of patient medical data, wherein each of the plurality of patient medical data comprises patient private health information, wherein access to patient medical data is restricted by each medical institution by limiting access to information that the medical institution considers privileged, wherein aggregating the plurality of patient medical data comprises storing the plurality of patient medical data in a searchable relational database, the patient medical data being arranged and stored to facilitate fast query, retrieval and analysis, wherein the patient private health information is stored in a separate set of restricted database tables for each medical institution, that are separate and isolated from other, unrestricted database tables in said searchable relational database containing the plurality of patient medical data;

receive a query for medical information pertaining to a particular medical condition applicable to a plurality of patients;

searching the other unrestricted database tables in the searchable relational database and extracting the medical information based on the query;

producing a result of the query based on the analyzing of the aggregated medical data, wherein the result of the query does not include any of the patient private health information from the restricted tables; and transmitting the result of the query.

* * * * *